United States Patent
Hu et al.

(10) Patent No.: US 9,828,345 B2
(45) Date of Patent: Nov. 28, 2017

(54) PHENYLPYRAZOLE DERIVATIVES AS POTENT ROCK1 AND ROCK2 INHIBITORS

(71) Applicant: BRISTOL-MYERS SQUIBB COMPANY, Princeton, NJ (US)

(72) Inventors: Zilun Hu, Jamison, PA (US); Mimi L. Quan, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/770,489

(22) PCT Filed: Feb. 28, 2014

(86) PCT No.: PCT/US2014/019242
§ 371 (c)(1),
(2) Date: Aug. 26, 2015

(87) PCT Pub. No.: WO2014/134391
PCT Pub. Date: Sep. 4, 2014

(65) Prior Publication Data
US 2016/0002172 A1 Jan. 7, 2016

Related U.S. Application Data

(60) Provisional application No. 61/770,531, filed on Feb. 28, 2013.

(51) Int. Cl.
| | | |
|---|---|---|
| C07D 231/12 | (2006.01) | |
| C07D 401/12 | (2006.01) | |
| C07D 471/04 | (2006.01) | |
| C07D 403/12 | (2006.01) | |
| C07D 409/12 | (2006.01) | |
| C07D 487/04 | (2006.01) | |

(52) U.S. Cl.
CPC ......... *C07D 231/12* (2013.01); *C07D 401/12* (2013.01); *C07D 403/12* (2013.01); *C07D 409/12* (2013.01); *C07D 471/04* (2013.01); *C07D 487/04* (2013.01)

(58) Field of Classification Search
None
See application file for complete search history.

(56) References Cited

U.S. PATENT DOCUMENTS

| | | | |
|---|---|---|---|
| 6,020,357 A | 2/2000 | Pinto et al. | |
| 6,121,271 A | 9/2000 | Dollings et al. | |
| 6,187,797 B1 | 2/2001 | Pruitt et al. | |
| 6,339,099 B1 | 1/2002 | Lam et al. | |
| 6,511,974 B1 | 1/2003 | Dusza et al. | |
| 6,984,735 B2 | 1/2006 | McKew et al. | |
| 7,041,693 B2 | 5/2006 | Sheppeck | |
| 7,101,883 B2 | 9/2006 | Maduskuie | |
| 7,166,619 B2 | 1/2007 | Li et al. | |
| 7,211,671 B2 | 5/2007 | Sheppeck et al. | |
| 7,282,588 B2 | 10/2007 | Dhanak et al. | |
| 7,468,446 B2 | 12/2008 | Muller et al. | |
| 7,485,658 B2 | 2/2009 | Bolger et al. | |
| 7,906,652 B2 | 3/2011 | Baker et al. | |
| 8,084,623 B2 | 12/2011 | Iyer et al. | |
| 8,288,405 B2 | 10/2012 | Bagley et al. | |
| 8,329,703 B2 | 12/2012 | Hu et al. | |
| 8,338,439 B2 | 12/2012 | Singh et al. | |
| 8,445,686 B2 | 5/2013 | Mack et al. | |
| 8,653,270 B2 | 2/2014 | Heidelbaugh et al. | |
| 8,916,565 B2 | 12/2014 | Hadida Ruah et al. | |
| 2004/0044041 A1 | 3/2004 | Kuduk et al. | |
| 2004/0082641 A1 | 4/2004 | Rytved et al. | |
| 2008/0306044 A1 | 12/2008 | Costanzo et al. | |
| 2009/0053192 A1 | 2/2009 | Millan et al. | |

FOREIGN PATENT DOCUMENTS

| | | |
|---|---|---|
| AR | 57450 A1 | 12/2007 |
| AU | 2012200157 A1 | 2/2012 |
| CN | 102451178 A | 5/2012 |
| DE | 19545878 | 6/1997 |

(Continued)

OTHER PUBLICATIONS

Al-Sha'er, M.A. et al., "Elaborate Ligand-Based Modeling Reveals New Nanomolar Heat Shock Protein 90α Inhibitors", J. Chem. Inf. Model., vol. 50, No. 9, pp. 1706-1723 (2010).

Ashek, A. et al., "A combined approach of docking and 3D QSAR study of β-ketoacyl-acyl carrier protein synthase III (FabH) inhibitors", Bioorganic & Medicinal Chemistry, vol. 14, pp. 1474-1482 (2006).

Ashek, A. et al., "HQSAR study of β-ketoacyl-acyl carrier protein synthase III (FabH) inhibitors", Journal of Enzyme Inhibition and Medicinal Chemistry, vol. 22, No. 1, pp. 7-14 (2007).

Desai, P.V. et al., "Identification of Novel Parasitic Cysteine Protease Inhibitors by Use of Virtual Screening. 2. The Available Chemical Directory", Journal of Medicinal Chemistry, vol. 49, No. 5, pp. 1576-1584 (2006).

Fang, X. et al., "Tetrahydroisoquinoline Derivatives as Highly Selective and Potent Rho Kinase Inhibitors", Journal of Medicinal Chemistry, vol. 53, No. 15, pp. 5727-5737 (2010).

(Continued)

*Primary Examiner* — Kamal Saeed
(74) *Attorney, Agent, or Firm* — Hong Liu

(57) ABSTRACT

The present invention provides compounds of Formula (I): (I) or stereoisomers, tautomers, or pharmaceutically acceptable salts thereof, wherein all the variables are as defined herein. These compounds are selective ROCK inhibitors. This invention also relates to pharmaceutical compositions comprising these compounds and methods of treating cardiovascular, smooth muscle, oncologic, neuropathologic, autoimmune, fibrotic, and/or inflammatory disorders using the same.

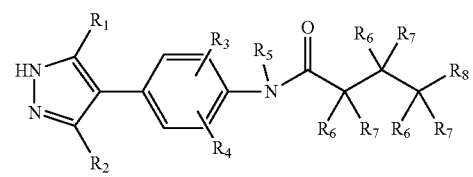

5 Claims, No Drawings

(56) References Cited

FOREIGN PATENT DOCUMENTS

| | | |
|---|---|---|
| EP | 0 742 200 A1 | 11/1996 |
| EP | 1 574 502 A1 | 9/2005 |
| EP | 2 002 838 A1 | 12/2008 |
| FR | 2 887 548 A1 | 12/2006 |
| FR | 2 888 237 A1 | 1/2007 |
| FR | 2 894 578 A1 | 6/2007 |
| FR | 2 894 579 A1 | 6/2007 |
| FR | 2 904 827 A1 | 2/2008 |
| FR | 2 911 136 A1 | 7/2008 |
| JP | 2000-109465 A | 4/2000 |
| JP | 2000109465 * | 4/2000 |
| JP | 2000-256358 A | 9/2000 |
| JP | 2004-161716 A | 6/2004 |
| JP | 2010-275302 A | 12/2010 |
| KR | 2009-0033583 A | 4/2009 |
| WO | WO 93/16036 A1 | 8/1993 |
| WO | WO 94/22826 A1 | 10/1994 |
| WO | WO 95/18097 A1 | 7/1995 |
| WO | WO 96/21660 A1 | 7/1996 |
| WO | WO 97/30971 A1 | 8/1997 |
| WO | WO 97/36886 A1 | 10/1997 |
| WO | WO 98/28269 A1 | 7/1998 |
| WO | WO 98/28282 A2 | 7/1998 |
| WO | WO 98/57937 A2 | 12/1998 |
| WO | WO 99/06403 A1 | 2/1999 |
| WO | WO 99/06409 A1 | 2/1999 |
| WO | WO 99/55663 A1 | 11/1999 |
| WO | WO 99/58522 A1 | 11/1999 |
| WO | WO 00/26197 A1 | 5/2000 |
| WO | WO 00/29399 A1 | 5/2000 |
| WO | WO 00/46224 A2 | 8/2000 |
| WO | WO 00/64888 A1 | 11/2000 |
| WO | WO 01/22969 A2 | 4/2001 |
| WO | WO 01/51456 A2 | 7/2001 |
| WO | WO 01/68605 A1 | 9/2001 |
| WO | WO 01/70671 A2 | 9/2001 |
| WO | WO 02/00651 A2 | 1/2002 |
| WO | WO 02/48099 A1 | 6/2002 |
| WO | WO 02/064558 A2 | 8/2002 |
| WO | WO 02/070462 A1 | 9/2002 |
| WO | WO 02/070483 A1 | 9/2002 |
| WO | WO 02/072558 A1 | 9/2002 |
| WO | WO 02/076959 A1 | 10/2002 |
| WO | WO 02/096426 A1 | 12/2002 |
| WO | WO 03/000653 A1 | 1/2003 |
| WO | WO 03/002559 A2 | 1/2003 |
| WO | WO 03/002561 A1 | 1/2003 |
| WO | WO 03/004474 A1 | 1/2003 |
| WO | WO 03/011854 A1 | 2/2003 |
| WO | WO 03/032991 A1 | 4/2003 |
| WO | WO 03/037887 A1 | 5/2003 |
| WO | WO 03/079986 A2 | 10/2003 |
| WO | WO 03/082826 A1 | 10/2003 |
| WO | WO 2004/000788 A1 | 12/2003 |
| WO | WO 2004/043926 A1 | 5/2004 |
| WO | WO 2004/071426 A2 | 8/2004 |
| WO | WO 2004/072025 A2 | 8/2004 |
| WO | WO 2004/092146 A2 | 10/2004 |
| WO | WO 2005/000813 A1 | 1/2005 |
| WO | WO 2005/012293 A1 | 2/2005 |
| WO | WO 2005/020921 A2 | 3/2005 |
| WO | WO 2005/021537 A1 | 3/2005 |
| WO | WO 2005/023809 A1 | 3/2005 |
| WO | WO 2005/039494 A2 | 5/2005 |
| WO | WO 2005/040110 A1 | 5/2005 |
| WO | WO 2005/074643 A2 | 8/2005 |
| WO | WO 2006/050097 A1 | 5/2006 |
| WO | WO 2006/068933 A2 | 6/2006 |
| WO | WO 2006/102645 A1 | 9/2006 |
| WO | WO 2007/002559 A1 | 1/2007 |
| WO | WO 2007/024922 A1 | 3/2007 |
| WO | WO 2007/075749 A2 | 7/2007 |
| WO | WO 2007/098169 A1 | 8/2007 |
| WO | WO 2007/146230 A2 | 12/2007 |
| WO | WO 2008/000643 A1 | 1/2008 |
| WO | WO 2008/003770 A1 | 1/2008 |
| WO | WO 2008/016643 A2 | 2/2008 |
| WO | WO 2008/028617 A1 | 3/2008 |
| WO | WO 2008/057246 A2 | 5/2008 |
| WO | WO 2008/064310 A2 | 5/2008 |
| WO | WO 2008/064317 A1 | 5/2008 |
| WO | WO 2008/064318 A2 | 5/2008 |
| WO | WO 2008/083124 A1 | 7/2008 |
| WO | WO 2008/088692 A2 | 7/2008 |
| WO | WO 2008/094473 A1 | 8/2008 |
| WO | WO 2008/099076 A2 | 8/2008 |
| WO | WO 2008/099804 A1 | 8/2008 |
| WO | WO 2008/137102 A2 | 11/2008 |
| WO | WO 2008/141731 A2 | 11/2008 |
| WO | WO 2008/147518 A1 | 12/2008 |
| WO | WO 2008/152138 A2 | 12/2008 |
| WO | WO 2008/155670 A2 | 12/2008 |
| WO | WO 2009/003998 A2 | 1/2009 |
| WO | WO 2009/015208 A1 | 1/2009 |
| WO | WO 2009/027392 A1 | 3/2009 |
| WO | WO 2009/036012 A1 | 3/2009 |
| WO | WO 2009/036051 A1 | 3/2009 |
| WO | WO 2009/052065 A1 | 4/2009 |
| WO | WO 2009/057811 A2 | 5/2009 |
| WO | WO 2009/061676 A2 | 5/2009 |
| WO | WO 2009/076352 A1 | 6/2009 |
| WO | WO 2009/079008 A1 | 6/2009 |
| WO | WO 2009/079009 A1 | 6/2009 |
| WO | WO 2009/079225 A1 | 6/2009 |
| WO | WO 2009/114994 A1 | 9/2009 |
| WO | WO 2009/126691 A1 | 10/2009 |
| WO | WO 2009/131173 A1 | 10/2009 |
| WO | WO 2009/137657 A1 | 11/2009 |
| WO | WO 2009/146648 A1 | 12/2009 |
| WO | WO 2009/158571 A1 | 12/2009 |
| WO | WO 2010/036316 A1 | 4/2010 |
| WO | WO 2010/039238 A1 | 4/2010 |
| WO | WO 2010/040274 A1 | 4/2010 |
| WO | WO 2010/075290 A1 | 7/2010 |
| WO | WO 2010/077624 A1 | 7/2010 |
| WO | WO 2010/080357 A1 | 7/2010 |
| WO | WO 2010/093849 A2 | 8/2010 |
| WO | WO 2010/129848 A1 | 11/2010 |
| WO | WO 2010/142752 A1 | 12/2010 |
| WO | WO 2010/144586 A1 | 12/2010 |
| WO | WO 2011/032169 A2 | 3/2011 |
| WO | WO 2011/041593 A1 | 4/2011 |
| WO | WO 2011/042797 A1 | 4/2011 |
| WO | WO 2011/042798 A1 | 4/2011 |
| WO | WO 2011/058473 A1 | 5/2011 |
| WO | WO 2011/067306 A1 | 6/2011 |
| WO | WO 2011/073376 A1 | 6/2011 |
| WO | WO 2011/078306 A1 | 6/2011 |
| WO | WO 2011/088027 A1 | 7/2011 |
| WO | WO 2011/088031 A2 | 7/2011 |
| WO | WO 2011/088181 A1 | 7/2011 |
| WO | WO 2011/090760 A1 | 7/2011 |
| WO | WO 2011/093501 A1 | 8/2011 |
| WO | WO 2011/099502 A1 | 8/2011 |
| WO | WO 2011/106632 A1 | 9/2011 |
| WO | WO 2011/112191 A1 | 9/2011 |
| WO | WO 2011/112769 A1 | 9/2011 |
| WO | WO 2011/140425 A1 | 11/2011 |
| WO | WO 2011/156557 A2 | 12/2011 |
| WO | WO 2012/006202 A1 | 1/2012 |
| WO | WO 2012/006203 A1 | 1/2012 |
| WO | WO 2012/022265 A1 | 2/2012 |
| WO | WO 2012/040444 A2 | 3/2012 |
| WO | WO 2012/051117 A2 | 4/2012 |
| WO | WO 2012/068210 A1 | 5/2012 |
| WO | WO 2012/069175 A1 | 5/2012 |
| WO | WO 2012/074067 A1 | 6/2012 |
| WO | WO 2012/074068 A1 | 6/2012 |
| WO | WO 2012/078593 A2 | 6/2012 |
| WO | WO 2012/080220 A1 | 6/2012 |
| WO | WO 2012/123745 A1 | 9/2012 |
| WO | WO 2012/135160 A1 | 10/2012 |
| WO | WO 2012/135697 A2 | 10/2012 |

(56) References Cited

FOREIGN PATENT DOCUMENTS

| | | |
|---|---|---|
| WO | WO 2012/146724 A2 | 11/2012 |
| WO | WO 2012/160218 A1 | 11/2012 |
| WO | WO 2012/160464 A1 | 11/2012 |
| WO | WO 2012/166389 A1 | 12/2012 |
| WO | WO 2013/007676 A1 | 1/2013 |
| WO | WO 2013/018526 A1 | 2/2013 |
| WO | WO 2013/022609 A1 | 2/2013 |
| WO | WO 2013/067248 A1 | 5/2013 |
| WO | WO 2014/031784 A1 | 2/2014 |
| WO | WO 2014/079850 A1 | 5/2014 |
| WO | WO 2014/113620 A2 | 7/2014 |
| WO | WO 2014/134388 A1 | 9/2014 |
| WO | WO 2015/002915 A1 | 1/2015 |
| WO | WO 2015/002926 A1 | 1/2015 |
| WO | WO 2015/107053 A1 | 7/2015 |

OTHER PUBLICATIONS

Gao, Z. et al., "Discovery of aryl ureas and aryl amides as potent and selective histamine $H_3$ receptor antagonists for the treatment of obesity (Part II)", Bioorganic & Medicinal Chemistry Letters, vol. 23, pp. 3421-3426 (2013).
Liang, J. et al., "Lead Optimization of a 4-Aminopyridine Benzamide Scaffold to Identify Potent, Selective, and Orally Bioavailable TYK2 Inhibitors", Journal of Medicinal Chemistry, vol. 56, pp. 4521-4536 (2013).
Nie, Z. et al., "Structure-Based Design, Synthesis, and Study of Potent Inhibitors of β-Ketoacyl-acyl Carrier Protein Synthase III as Potential Antimicrobial Agents", Journal of Medicinal Chemistry, vol. 48, No. 5, pp. 1596-1609 (2005).
Singh, S. et al., "QSAR studies on benzoylaminobenzoic acid derivatives as inhibitors of β-ketoacyl-acyl carrier protein synthase III", European Journal of Medicinal Chemistry, vol. 43, pp. 1071-1080 (2008).
Watterson, S.H. et al., "Novel Amide-Based Inhibitors of Inosine 5'-Monophosphate Dehydrogenase", Bioorganic & Medicinal Chemistry Letters, vol. 12, pp. 2879-2882 (2002).
Yang, N. et al., "A Three-Dimensional Pharmacophore Model for IMPDH Inhibitors", Chem. Biol. Drug Des., vol. 78, pp. 175-182 (2011).
Yu, M. et al., "Identification of piperazine-bisamide GHSR antagonists for the treatment of obesity", Bioorganic & Medicinal Chemistry Letters, vol. 20, pp. 1758-1762 (2010).
CAS Registry No. 332109-19-0, Entered STN: Apr. 24, 2001.
CAS Registry No. 871346-25-7, Entered STN: Jan. 6, 2006.
CAS Registry No. 871346-26-8, Entered STN: Jan. 6, 2006.
CAS Registry No. 871346-27-9, Entered STN: Jan. 6, 2006.
CAS Registry No. 871346-28-0, Entered STN: Jan. 6, 2006.
CAS Registry No. 871346-31-5, Entered STN: Jan. 6, 2006.
CAS Registry No. 883944-19-2, Entered STN: May 12, 2006.
CAS Registry No. 957625-34-2, Entered STN: Dec. 12, 2007.
CAS Registry No. 957625-55-7, Entered STN: Dec. 12, 2007.
CAS Registry No. 957625-86-4, Entered STN: Dec. 12, 2007.
CAS Registry No. 957626-02-7, Entered STN: Dec. 12, 2007.
CAS Registry No. 957626-22-1, Entered STN: Dec. 12, 2007.
CAS Registry No. 957659-72-2, Entered STN: Dec. 12, 2007.
CAS Registry No. 957948-51-5, Entered STN: Dec. 13, 2007.
CAS Registry No. 957948-53-7, Entered STN: Dec. 13, 2007.
CAS Registry No. 957948-63-9, Entered STN: Dec. 13, 2007.
CAS Registry No. 957948-66-2, Entered STN: Dec. 13, 2007.
CAS Registry No. 957948-79-7, Entered STN: Dec. 13, 2007.
CAS Registry No. 957948-89-9, Entered STN: Dec. 13, 2007.
CAS Registry No. 957949-01-8, Entered STN: Dec. 13, 2007.
CAS Registry No. 957949-04-1, Entered STN: Dec. 13, 2007.
CAS Registry No. 957949-08-5, Entered STN: Dec. 13, 2007.
CAS Registry No. 957969-51-6, Entered STN: Dec. 14, 2007.
CAS Registry No. 958514-88-0, Entered STN: Dec. 18, 2007.
CAS Registry No. 1007478-21-8, Entered STN: Mar. 12, 2008.
CAS Registry No. 1007478-26-3, Entered STN: Mar. 12, 2008.
CAS Registry No. 1007478-31-0, Entered STN: Mar. 12, 2008.
CAS Registry No. 1007516-52-0, Entered STN: Mar. 12, 2008.
CAS Registry No. 1022141-29-2, Entered STN: May 23, 2008.
CAS Registry No. 1022149-04-7, Entered STN: May 23, 2008.
CAS Registry No. 1022389-37-2, Entered STN: May 25, 2008.
CAS Registry No. 1022391-13-4, Entered STN: May 25, 2008.
CAS Registry No. 1022410-03-2, Entered STN: May 25, 2008.
CAS Registry No. 1022477-68-4, Entered STN: May 25, 2008.
CAS Registry No. 1022501-96-7, Entered STN: May 25, 2008.
CAS Registry No. 1022511-27-8, Entered STN: May 25, 2008.
CAS Registry No. 1022548-38-4, Entered STN: May 26, 2008.
CAS Registry No. 1022555-87-8, Entered STN: May 26, 2008.
CAS Registry No. 1022605-84-0, Entered STN: May 26, 2008.
CAS Registry No. 1022862-24-3, Entered STN: May 27, 2008.
CAS Registry No. 1022867-13-5, Entered STN: May 27, 2008.
CAS Registry No. 1022885-61-5, Entered STN: May 27, 2008.
CAS Registry No. 1023030-61-6, Entered STN: May 27, 2008.
CAS Registry No. 1023032-12-3, Entered STN: May 27, 2008.
CAS Registry No. 1023210-76-5, Entered STN: May 28, 2008.
CAS Registry No. 1023229-07-3, Entered STN: May 28, 2008.
CAS Registry No. 1023246-20-9, Entered STN: May 28, 2008.
CAS Registry No. 1023256-02-1, Entered STN: May 28, 2008.
CAS Registry No. 1023259-66-6, Entered STN: May 28, 2008.
CAS Registry No. 1023268-55-4, Entered STN: May 28, 2008.
CAS Registry No. 1023363-81-6, Entered STN: May 28, 2008.
CAS Registry No. 1023417-95-9, Entered STN: May 28, 2008.
CAS Registry No. 1023420-66-7, Entered STN: May 28, 2008.
CAS Registry No. 1023429-59-5, Entered STN: May 28, 2008.
CAS Registry No. 1023448-24-9, Entered STN: May 29, 2008.
CAS Registry No. 1023478-48-9, Entered STN: May 29, 2008.
CAS Registry No. 1023478-49-0, Entered STN: May 29, 2008.
CAS Registry No. 1023482-12-3, Entered STN: May 29, 2008.
CAS Registry No. 1023502-09-1, Entered STN: May 29, 2008.
CAS Registry No. 1023502-84-2, Entered STN: May 29, 2008.
CAS Registry No. 1023504-48-4, Entered STN: May 29, 2008.
CAS Registry No. 1023510-19-1, Entered STN: May 29, 2008.
CAS Registry No. 1023531-41-0, Entered STN: May 29, 2008.
CAS Registry No. 1023531-42-1, Entered STN: May 29, 2008.
CAS Registry No. 1023531-45-4, Entered STN: May 29, 2008.
CAS Registry No. 1023531-46-5, Entered STN: May 29, 2008.
CAS Registry No. 1023531-65-8, Entered STN: May 29, 2008.
CAS Registry No. 1023532-30-0, Entered STN: May 29, 2008.
CAS Registry No. 1023558-47-5, Entered STN: May 29, 2008.
CAS Registry No. 1023568-84-4, Entered STN: May 29, 2008.
CAS Registry No. 1023577-42-5, Entered STN: May 29, 2008.
CAS Registry No. 1023579-52-3, Entered STN: May 29, 2008.
CAS Registry No. 1023589-88-9, Entered STN: May 29, 2008.
CAS Registry No. 1023804-70-7, Entered STN: May 30, 2008.
CAS Registry No. 1023820-69-0, Entered STN: May 30, 2008.
CAS Registry No. 1023831-23-3, Entered STN: May 30, 2008.
CAS Registry No. 1023837-66-2, Entered STN: May 30, 2008.
CAS Registry No. 1023845-13-7, Entered STN: May 30, 2008.
CAS Registry No. 1023845-17-1, Entered STN: May 30, 2008.
CAS Registry No. 1023846-53-8, Entered STN: May 30, 2008.
CAS Registry No. 1023851-62-8, Entered STN: May 30, 2008.
CAS Registry No. 1023881-64-2, Entered STN: May 30, 2008.
CAS Registry No. 1024047-18-4, Entered STN: May 30, 2008.
CAS Registry No. 1024073-24-2, Entered STN: May 30, 2008.
CAS Registry No. 1024113-66-3, Entered STN: Jun. 1, 2008.
CAS Registry No. 1024121-76-3, Entered STN: Jun. 1, 2008.
CAS Registry No. 1024126-88-2, Entered STN: Jun. 1, 2008.
CAS Registry No. 1024151-82-3, Entered STN: Jun. 1, 2008.
CAS Registry No. 1024164-97-3, Entered STN: Jun. 1, 2008.
CAS Registry No. 1024167-54-1, Entered STN: Jun. 1, 2008.
CAS Registry No. 1024175-63-0, Entered STN: Jun. 1, 2008.
CAS Registry No. 1024179-86-9, Entered STN: Jun. 1, 2008.
CAS Registry No. 1024198-56-8, Entered STN: Jun. 1, 2008.
CAS Registry No. 1024224-26-7, Entered STN: Jun. 1, 2008.
CAS Registry No. 1024234-57-8, Entered STN: Jun. 1, 2008.
CAS Registry No. 1024243-98-8, Entered STN: Jun. 1, 2008.
CAS Registry No. 1024410-77-2, Entered STN: Jun. 1, 2008.
CAS Registry No. 1024417-81-9, Entered STN: Jun. 1, 2008.
CAS Registry No. 1024461-95-7, Entered STN: Jun. 1, 2008.
CAS Registry No. 1024525-01-6, Entered STN: Jun. 1, 2008.

(56) References Cited

OTHER PUBLICATIONS

CAS Registry No. 1024580-07-1, Entered STN: Jun. 1, 2008.
CAS Registry No. 1090891-17-0, Entered STN: Dec. 28, 2008.
CAS Registry No. 1104200-98-7, Entered STN: Feb. 11, 2009.
CAS Registry No. 1104476-54-1, Entered STN: Feb. 11, 2009.
CAS Registry No. 1111447-17-6, Entered STN: Feb. 25, 2009.
CAS Registry No. 1197573-90-2, Entered STN: Dec. 16, 2009.
CAS Registry No. 1202016-27-0, Entered STN: Jan. 13, 2010.
CAS Registry No. 1210002-45-1, Entered STN: Mar. 15, 2010.
CAS Registry No. 1210912-02-9, Entered STN: Mar. 17, 2010.
CAS Registry No. 1222783-52-9, Entered STN: May 13, 2010.
CAS Registry No. 1241174-10-6, Entered STN: Sep. 15, 2010.
CAS Registry No. 1241306-75-1, Entered STN: Sep. 15, 2010.
CAS Registry No. 1258705-85-9, Entered STN: Jan. 7, 2011.
CAS Registry No. 1258743-53-1, Entered STN: Jan. 7, 2011.
CAS Registry No. 1259127-20-2, Entered STN: Jan. 12, 2011.
CAS Registry No. 1259162-21-4, Entered STN: Jan. 12, 2011.
CAS Registry No. 1278338-39-8, Entered STN: Apr. 11, 2011.
CAS Registry No. 1278338-66-1, Entered STN: Apr. 11, 2011.
CAS Registry No. 1278879-14-3, Entered STN: Apr. 12, 2011.
CAS Registry No. 1279552-97-4, Entered STN: Apr. 13, 2011.
CAS Registry No. 1279831-29-6, Entered STN: Apr. 14, 2011.
CAS Registry No. 1279831-30-9, Entered STN: Apr. 14, 2011.
CAS Registry No. 1279928-19-6, Entered STN: Apr. 14, 2011.
CAS Registry No. 1280864-26-7, Entered STN: Apr. 17, 2011.
CAS Registry No. 1280889-49-7, Entered STN: Apr. 17, 2011.
CAS Registry No. 1281168-57-7, Entered STN: Apr. 17, 2011.
CAS Registry No. 1287595-92-9, Entered STN: Apr. 29, 2011.
CAS Registry No. 1289299-22-4, Entered STN: May 3, 2011.
CAS Registry No. 1289301-34-3, Entered STN: May 3, 2011.
CAS Registry No. 1289302-16-4, Entered STN: May 3, 2011.
CAS Registry No. 1289833-66-4, Entered STN: May 4, 2011.
CAS Registry No. 1289937-35-4, Entered STN: May 4, 2011.
CAS Registry No. 1290549-19-7, Entered STN: May 5, 2011.
CAS Registry No. 1290602-24-2, Entered STN: May 5, 2011.
CAS Registry No. 1293886-01-7, Entered STN: May 12, 2011.
CAS Registry No. 1294251-73-2, Entered STN: May 13, 2011.
CAS Registry No. 1294981-04-6, Entered STN: May 15, 2011.
CAS Registry No. 1295073-12-9, Entered STN: May 15, 2011.
CAS Registry No. 1297434-86-6, Entered STN: May 19, 2011.
CAS Registry No. 1297435-04-1, Entered STN: May 19, 2011.
CAS Registry No. 1297890-23-3, Entered STN: May 20, 2011.
CAS Registry No. 1297890-68-6, Entered STN: May 20, 2011.
CAS Registry No. 1298114-74-5, Entered STN: May 20, 2011.
CAS Registry No. 1298534-85-6, Entered STN: May 22, 2011.
CAS Registry No. 1299164-16-1, Entered STN: May 24, 2011.
CAS Registry No. 1299262-67-1, Entered STN: May 24, 2011.
CAS Registry No. 1299322-06-7, Entered STN: May 24, 2011.
CAS Registry No. 1299344-37-8, Entered STN: May 24, 2011.
CAS Registry No. 1299906-56-1, Entered STN: May 24, 2011.
CAS Registry No. 1300200-25-2, Entered STN: May 25, 2011.
CAS Registry No. 1301108-77-9, Entered STN: May 26, 2011.
CAS Registry No. 1301467-59-3, Entered STN: May 27, 2011.
CAS Registry No. 1301469-78-2, Entered STN: May 27, 2011.
CAS Registry No. 1301472-22-9, Entered STN: May 27, 2011.
CAS Registry No. 1302687-23-5, Entered STN: May 30, 2011.
CAS Registry No. 1316419-52-9, Entered STN: Aug. 12, 2011.
CAS Registry No. 1318070-95-9, Entered STN: Aug. 15, 2011.
CAS Registry No. 1319542-14-7, Entered STN: Aug. 18, 2011.
CAS Registry No. 1319829-50-9, Entered STN: Aug. 19, 2011.
CAS Registry No. 1319940-03-8, Entered STN: Aug. 19, 2011.
CAS Registry No. 1322479-65-1, Entered STN: Aug. 24, 2011.
CAS Registry No. 1332104-46-7, Entered STN: Sep. 14, 2011.
CAS Registry No. 1332124-00-1, Entered STN: Sep. 14, 2011.
CAS Registry No. 1332124-75-0, Entered STN: Sep. 14, 2011.
CAS Registry No. 1332152-60-9, Entered STN: Sep. 14, 2011.
CAS Registry No. 1332159-43-9, Entered STN: Sep. 14, 2011.
CAS Registry No. 1332197-27-9, Entered STN: Sep. 14, 2011.
CAS Registry No. 1332208-87-3, Entered STN: Sep. 14, 2011.
CAS Registry No. 1351066-78-8, Entered STN: Dec. 16, 2011.
CAS Registry No. 1351273-71-6, Entered STN: Dec. 19, 2011.
CAS Registry No. 1355818-21-1, Entered STN: Feb. 8, 2012.
CAS Registry No. 1375222-56-2, Entered STN: Jun. 5, 2012.
CAS Registry No. 1376313-29-9, Entered STN: Jun. 7, 2012.

* cited by examiner

PHENYLPYRAZOLE DERIVATIVES AS POTENT ROCK1 AND ROCK2 INHIBITORS

CROSS REFERENCES TO RELATED APPLICATIONS

This application is a 371 application of PCT/US2014/019242, filed Feb. 28, 2014, which claims priority from U.S. Provisional Application Ser. No. 61/770,531 filed Feb. 28, 2013 which are incorporated by reference herein in their entirety.

FIELD OF THE INVENTION

The present invention relates to novel phenylpyrazole derivatives, compositions containing them, and methods of using them, for example, for the treatment or prophylaxis of disorders associated with aberrant Rho kinase activity.

BACKGROUND OF THE INVENTION

Rho-Kinase (ROCK) is a member of the serine-threonine protein kinase family. ROCK exists in two isoforms, ROCK1 and ROCK2 (Ishizaki, T. et al., *EMBO J.*, 15:1885-1893 (1996)). ROCK has been identified as an effector molecule of RhoA, a small GTP-binding protein (G protein) that plays a key role in multiple cellular signaling pathways. ROCK and RhoA are ubiquitously expressed across tissues. The RhoA/ROCK signaling pathway is involved in a number of cellular functions, such as actin organization, cell adhesion, cell migration, and cytokinesis (Riento, K. et al., *Nat. Rev. Mol. Cell Biol.*, 4:446-456 (2003)). It is also directly involved in regulating smooth muscle contraction (Somlyo, A. P., *Nature*, 389:908-911 (1997)). Upon activation of its receptor, RhoA is activated, and, in turn, it activates ROCK. Activated ROCK phosphorylates the myosin-binding subunit of myosin light chain phosphatase, which inhibits activity of the phosphatase and leads to contraction. Contraction of the smooth muscle in the vasculature increases blood pressure, leading to hypertension.

There is considerable evidence in the literature that the Rho A/ROCK signaling pathway plays an important role in signal transduction initiated by several vasoactive factors, for example angiotensin II (Yamakawa, T. et al., *Hypertension*, 35:313-318 (2000)), urotension II (Sauzeau, V. et al., *Circ. Res.*, 88:1102-1104 (2001)), endothelin-1 (Tangkijvanich, P. et al., *Hepatology*, 33:74-80 (2001)), serotonin (Shimokawa, H., *Jpn. Circ. J.*, 64:1-12 (2000)), norepinephrine (Martinez, M. C. et al., *Am. J. Physiol.*, 279:H1228-H1238 (2000)) and platelet-derived growth factor (PDGF) (Kishi, H. et al., *J. Biochem.*, 128:719-722 (2000)). Many of these factors are implicated in the pathogenesis of cardiovascular disease.

Additional studies in the literature, some using the known ROCK inhibitors fasudil (Asano, T. et al., *J. Pharmacol. Exp. Ther.*, 241:1033-1040 (1987)) or Y-27632 (Uehata, M. et al., *Nature*, 389:990-994 (1997)) further illustrate the link between ROCK and cardiovascular disease. For example, ROCK expression and activity have been shown to be elevated in spontaneously hypertensive rats, suggesting a link to the development of hypertension in these animals (Mukai, Y. et al., *FASEB J.*, 15:1062-1064 (2001)). The ROCK inhibitor Y-27632 (Uehata, M. et al., *Nature*, ibid.) was shown to significantly decrease blood pressure in three rat models of hypertension, including the spontaneously hypertensive rat, renal hypertensive rat and deoxycortisone acetate salt hypertensive rat models, while having only a minor effect on blood pressure in control rats. This reinforces the link between ROCK and hypertension.

Other studies suggest a link between ROCK and atherosclerosis. For example, gene transfer of a dominant negative form of ROCK suppressed neointimal formation following balloon injury in porcine femoral arteries (Eto, Y. et al., *Am. J. Physiol. Heart Circ. Physiol.*, 278:H1744-H1750 (2000)). In a similar model, ROCK inhibitor Y-27632 also inhibited neointimal formation in rats (Sawada, N. et al., *Circulation*, 101:2030-2033 (2000)). In a porcine model of IL-1 beta-induced coronary stenosis, long term treatment with the ROCK inhibitor fasudil was shown to progressively reduce coronary stenosis, as well as promote a regression of coronary constrictive remodeling (Shimokawa, H. et al., *Cardiovascular Res.*, 51:169-177 (2001)).

Additional investigations suggest that a ROCK inhibitor would be useful in treating other cardiovascular diseases. For example, in a rat stroke model, fasudil was shown to reduce both the infarct size and neurologic deficit (Toshima, Y., *Stroke*, 31:2245-2250 (2000)). The ROCK inhibitor Y-27632 was shown to improve ventricular hypertrophy, fibrosis and function in a model of congestive heart failure in Dahl salt-sensitive rats (Kobayashi, N. et al., *Cardiovascular Res.*, 55:757-767 (2002)).

Other animal or clinical studies have implicated ROCK in additional diseases including coronary vasospasm (Shimokawa, H. et al., *Cardiovasc. Res.*, 43:1029-1039 (1999)), cerebral vasospasm (Sato, M. et al., *Circ. Res.*, 87:195-200 (2000)), ischemia/reperfusion injury (Yada, T. et al., *J. Am. Coll. Cardiol.*, 45:599-607 (2005)), pulmonary hypertension (Fukumoto, Y. et al., *Heart*, 91:391-392 (2005)), angina (Shimokawa, H. et al., *J. Cardiovasc. Pharmacol.*, 39:319-327 (2002)), renal disease (Satoh, S. et al., *Eur. J. Pharmacol.*, 455:169-174 (2002)) and erectile dysfunction (Gonzalez-Cadavid, N. F. et al., *Endocrine*, 23:167-176 (2004)).

In another study, it has been demonstrated that inhibition of the RhoA/ROCK signaling pathway allows formation of multiple competing lamellipodia that disrupt the productive migration of monocytes (Worthylake, R. A. et al., *J. Biol. Chem.*, 278:13578-13584 (2003)). It has also been reported that small molecule inhibitors of Rho Kinase are capable of inhibiting MCP-1 mediated chemotaxis in vitro (Iijima, H., *Bioorg. Med. Chem.*, 15:1022-1033 (2007)). Due to the dependence of immune cell migration upon the RhoA/ROCK signaling pathway one would anticipate inhibition of Rho Kinase should also provide benefit for diseases such as rheumatoid arthritis, psoriasis, and inflammatory bowel disease.

The above studies provide evidence for a link between ROCK and cardiovascular diseases including hypertension, atherosclerosis, restenosis, stroke, heart failure, coronary vasospasm, cerebral vasospasm, ischemia/reperfusion injury, pulmonary hypertension and angina, as well as renal disease and erectile dysfunction. Given the demonstrated effect of ROCK on smooth muscle, ROCK inhibitors may also be useful in other diseases involving smooth muscle hyper-reactivity, including asthma and glaucoma (Shimokawa, H. et al., *Arterioscler. Thromb. Vasc. Biol.*, 25:1767-1775 (2005)). Furthermore, Rho-kinase has been indicated as a drug target for the treatment of various other diseases, including airway inflammation and hyperresponsiveness (Henry, P. J. et al., *Pulm. Pharmacol. Ther.*, 18:67-74 (2005)), cancer (Rattan, R. et al., *J. Neurosci. Res.*, 83:243-255 (2006); Lepley, D. et al., *Cancer Res.*, 65:3788-3795 (2005)), fibrotic diseases (Jiang, C. et al., *Int. J. Mol. Sci.*, 13:8293-8307 (2012); Zhou, L. et al., *Am. J. Nephrol.*, 34:468-475 (2011)), as well as neurological disorders, such as spinal-cord injury, Alzheimer disease, multiple sclerosis, stroke and neuropathic pain (Mueller, B. K. et al., *Nat. Rev. Drug Disc.*, 4:387-398 (2005); Sun, X. et. al., *J. Neuroimmunol.*, 180:126-134 (2006)).

There remains an unmet medical need for new drugs to treat cardiovascular disease. In the 2012 update of Heart Disease and Stroke Statistics from the American Heart Association (*Circulation*, 125:e2-e220 (2012)), it was reported that cardiovascular disease accounted for 32.8% of all deaths in the US, with coronary heart disease accounting for ~1 in 6 deaths overall in the US. Contributing to these numbers, it was found that ~33.5% of the adult US population was hypertensive, and it was estimated that in 2010 ~6.6 million US adults would have heart failure. Therefore, despite the number of medications available to treat cardiovascular diseases (CVD), including diuretics, beta blockers, angiotensin converting enzyme inhibitors, angiotensin blockers and calcium channel blockers, CVD remains poorly controlled or resistant to current medication for many patients.

Although there are many reports of ROCK inhibitors under investigation (see, for example, US 2008/0275062 A1), fasudil is the only marketed ROCK inhibitor at this time. An i.v. formulation was approved in Japan for treatment of cerebral vasospasm. There remains a need for new therapeutics, including ROCK inhibitors, for the treatment of cardiovascular diseases, cancer, neurological diseases, renal diseases, fibrotic diseases, bronchial asthma, erectile dysfunction, and glaucoma.

SUMMARY OF THE INVENTION

The present invention provides novel phenylpyrazole derivatives including stereoisomers, tautomers, pharmaceutically acceptable salts, or solvates thereof, which are useful as selective inhibitors of Rho kinases.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of conditions associated with aberrant ROCK activity.

The compounds of the present invention may be used in therapy.

The compounds of the present invention may be used for the manufacture of a medicament for the treatment and/or prophylaxis of a condition associated with aberrant ROCK activity.

In another aspect, the present invention is directed to a method of treating a cardiovascular or related disease which method comprises administering to a patient in need of such treatment a compound of the present invention as described above. Examples of such diseases that may be treated include, for example, hypertension, atherosclerosis, restenosis, stroke, heart failure, renal failure, coronary artery disease, peripheral artery disease, coronary vasospasm, cerebral vasospasm, ischemia/reperfusion injury, pulmonary hypertension, angina, erectile dysfunction and renal disease.

In another aspect, the present invention is directed to a method of treating diseases involving smooth muscle hyper reactivity including asthma, erectile dysfunction and glaucoma, which method comprises administering to a patient in need of such treatment a compound of the present invention as described above.

In another aspect, the present invention is directed to a method of treating diseases mediated at least partially by Rho kinase including fibrotic diseases, oncology, spinal-cord injury, Alzheimer's disease, multiple sclerosis, stroke, neuropathic pain, rheumatoid arthritis, psoriasis and inflammatory bowel disease, which method comprises administering to a patient in need of such treatment a compound of the present invention as described above.

In yet additional aspects, the present invention is directed at pharmaceutical compositions comprising the above-mentioned compounds, processes for preparing the above-mentioned compounds and intermediates used in these processes.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

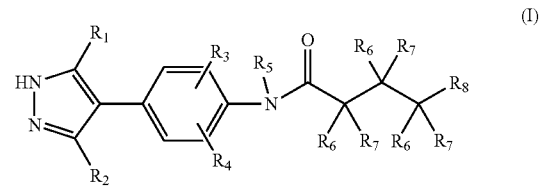

or stereoisomers, tautomers, pharmaceutically acceptable salts, solvates, or prodrugs thereof, wherein:

$R_1$ is independently selected from H, F, Cl, Br, OH, CN, $NR_aR_a$, —$OC_{1-4}$ alkyl substituted with 0-3 $R_e$, and $C_{1-4}$ alkyl substituted with 0-3 $R_e$;

$R_2$ is independently selected from H, —$(CH_2)_rOR_b$, —$(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rC(=O)(CH_2)_rNR_aR_a$, —$(CH_2)_rCN$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, —$(CH_2)_r$—$C_{3-6}$ carbocyclyl substituted with 0-3 $R_e$, and —$(CH_2)_r$-heterocyclyl substituted with 0-3 $R_e$;

$R_3$ is independently selected from H, —$(CH_2)_rOR_b$, —$(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rC(=O)(CH_2)_rNR_aR_a$, —$(CH_2)_rCN$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, —$(CH_2)_r$—$C_{3-6}$ carbocyclyl substituted with 0-3 $R_e$, and —$(CH_2)_r$-heterocyclyl substituted with 0-3 $R_e$;

$R_4$ is independently selected from H, F, Cl, Br, OH, CN, $OC_{1-4}$ alkyl substituted with 0-3 $R_c$, and $C_{1-4}$ alkyl substituted with 0-3 $R_e$;

R$_5$ is independently selected from H and C$_{1-4}$ alkyl substituted with 0-3 R$_e$;

R$_6$ and R$_7$ are independently selected from H, C$_{1-4}$alkyl substituted with 0-4 R$_e$, —(CH$_2$)$_r$OR$_b$, —(CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O) NR$_a$R$_a$, —(CH$_2$)$_r$C(=O)(CH$_2$)$_r$NR$_a$R$_a$, —(CH$_2$)$_r$NR$_a$C (=O)R$_b$, —(CH$_2$)$_r$NR$_a$C(=O)OR$_b$, —(CH$_2$)$_r$OC(=O) NR$_a$R$_a$, —(CH$_2$)$_r$NR$_a$C(=O)NR$_a$R$_a$, —(CH$_2$)$_r$C(=O) OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)—C$_{3-6}$ carbocyclyl substituted with 0-3 R$_e$, and —(CH$_2$)$_r$-heterocyclyl substituted with 0-3 R$_e$;

alternatively, R$_6$ and R$_7$ together with the carbon atom to which they are both attached form a cycloalkyl substituted with 0-5 R$_e$; alternatively, two adjacent R$_6$ groups may also form a cycloalkyl substituted with 0-5 R$_e$;

R$_8$ is independently selected from carbocyclyl and heterocyclyl, each substituted with 0-5 R$_9$;

R$_9$ is independently selected from F, Cl, Br, C$_{1-4}$alkyl, C$_{2-4}$alkenyl, C$_{2-4}$alkynyl, nitro, —(CHR$_d$)$_r$S(O)$_p$R$_c$, —(CHR$_d$)$_r$S(O)$_p$NR$_a$R$_a$, —(CHR$_d$)$_r$NR$_a$S(O)$_p$R$_c$, —(CHR$_d$)$_r$OR$_b$, —(CHR$_d$)$_r$CN, —(CHR$_d$)$_r$NR$_a$R$_a$, —(CHR$_d$)$_r$NR$_a$C(=O)R$_b$, —(CHR$_d$)$_r$NR$_a$C(=O) NR$_a$R$_a$, —(CHR$_d$)$_r$C(=O)OR$_b$, —(CHR$_d$)$_r$C(=O)R$_b$, —(CHR$_d$)$_r$ OC(=O)R$_b$, —(CHR$_d$)$_r$C(=O)NR$_a$R$_a$, —(CHR$_d$)$_r$-cycloalkyl, —(CHR$_d$)$_r$-heterocyclyl, —(CHR$_d$)$_r$-aryl, and —(CHR$_d$)$_r$-heteroaryl, wherein said alkyl, cycloalkyl, heterocyclyl, aryl, or heteroaryl is substituted with 0-4 R$_e$;

alternatively, two adjacent R$_9$ groups are combined to form a carbocyclic or heterocyclic ring comprising carbon atoms and 1-3 hetero atoms selected from N, O, and S(O)$_p$, wherein the carbocyclic and heterocyclic rings are substituted with 0-4 R$_e$;

R$_a$, at each occurrence, is independently selected from H, CN, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$; or R$_a$ and R$_a$ together with the nitrogen atom to which they are both attached form a heterocyclic ring substituted with 0-5 R$_e$;

R$_b$, at each occurrence, is independently selected from H, C$_{1-6}$ alkyl substituted with 0-5 R$_e$, C$_{2-6}$ alkenyl substituted with 0-5 R$_e$, C$_{2-6}$ alkynyl substituted with 0-5 R$_e$, —(CH$_2$)$_r$—C$_{3-10}$carbocyclyl substituted with 0-5 R$_e$, and —(CH$_2$)$_r$-heterocyclyl substituted with 0-5 R$_e$;

R$_c$, at each occurrence, is independently selected from C$_{1-6}$ alkyl substituted with 0-5 R$_e$, C$_{2-6}$ alkenyl substituted with 0-5 R$_e$, C$_{2-6}$alkynyl substituted with 0-5 R$_e$, C$_{3-6}$carbocyclyl, and heterocyclyl;

R$_d$, at each occurrence, is independently selected from H and C$_{1-4}$alkyl substituted with 0-5 R$_e$;

R$_e$, at each occurrence, is independently selected from C$_{1-6}$ alkyl substituted with 0-5 R$_f$, C$_{2-6}$ alkenyl, C$_{2-6}$ alkynyl, —(CH$_2$)$_r$—C$_{3-6}$ cycloalkyl, F, Cl, Br, CN, NO$_2$, =O, CO$_2$H, —(CH$_2$)$_r$OC$_{1-5}$ alkyl, —(CH$_2$)$_r$OR$_f$, S(O)$_p$R$_f$, C(=O)NR$_f$R$_f$, S(O)$_p$NR$_f$R$_f$, and —(CH$_2$)$_r$NR$_f$R$_f$;

R$_f$, at each occurrence, is independently selected from H, C$_{1-5}$alkyl, C$_{3-6}$ cycloalkyl, and phenyl, or R$_f$ and R$_f$ together with the nitrogen atom to which they are both attached form a heterocyclic ring optionally substituted with C$_{1-4}$alkyl;

p, at each occurrence, is independently selected from zero, 1, and 2; and r, at each occurrence, is independently selected from zero, 1, 2, 3, and 4.

In another aspect, the present invention provides compounds of Formula (II):

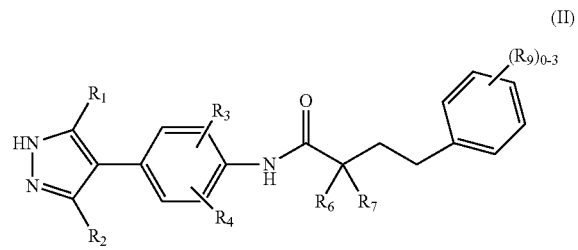

(II)

or stereoisomers, tautomers, pharmaceutically acceptable salts, solvates, or prodrugs thereof, wherein:

R$_1$ is independently selected from H, F, Cl, Br, OH, CN, NR$_a$R$_a$, and C$_{1-4}$ alkyl substituted with 0-3 R$_e$;

R$_2$ is independently selected from H, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$CN, —(CH$_2$)$_r$NR$_a$C (=O)R$_b$, —(CH$_2$)$_r$NR$_a$C(=O)OR$_b$, —(CH$_2$)$_r$OC(=O) NR$_a$R$_a$, —(CH$_2$)$_r$NR$_a$C(=O)NR$_a$R$_a$, —(CH$_2$)$_r$C(=O) OR$_b$, —(CH$_2$)$_r$S(O)$_p$NR$_a$R$_a$, —(CH$_2$)$_r$—C$_{3-6}$ carbocyclyl substituted with 0-3 R$_e$, and —(CH$_2$)$_r$-heterocyclyl substituted with 0-3 R$_e$;

R$_3$ is independently selected from H, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$CN, —(CH$_2$)$_r$NR$_a$C (=O)R$_b$, —(CH$_2$)$_r$NR$_a$C(=O)OR$_b$, —(CH$_2$)$_r$OC(=O) NR$_a$R$_a$, —(CH$_2$)$_r$NR$_a$C(=O)NR$_a$R$_a$, —(CH$_2$)$_r$C(=O) OR$_b$, —(CH$_2$)$_r$S(O)$_p$NR$_a$R$_a$, —(CH$_2$)$_r$—C$_{3-6}$ carbocyclyl substituted with 0-3 R$_e$, and —(CH$_2$)$_r$-heterocyclyl substituted with 0-3 R$_e$;

R$_4$ is independently selected from H, F, Cl, Br, OH, CN, and C$_{1-4}$ alkyl substituted with 0-3 R$_e$;

R$_6$ and R$_7$ are independently selected from H, C$_{1-4}$alkyl substituted with 0-4 R$_e$, —(CH$_2$)$_r$OR$_b$, —(CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O) NR$_a$R$_a$, —(CH$_2$)$_r$C(=O)(CH$_2$)$_r$NR$_a$R$_a$, —(CH$_2$)$_r$NR$_a$C (=O)R$_b$, —(CH$_2$)$_r$NR$_a$C(=O)OR$_b$, —(CH$_2$)$_r$OC(=O) NR$_a$R$_a$, —(CH$_2$)$_r$NR$_a$C(=O)NR$_a$R$_a$, —(CH$_2$)$_r$C(=O) OR$_b$, —(CH$_2$)$_r$S(O)$_p$NR$_a$R$_a$, —(CH$_2$)$_r$NR$_a$S(O)$_p$NR$_a$R$_a$, —(CH$_2$)$_r$NR$_a$S(O)$_p$R$_c$, (CH$_2$)$_r$—C$_{3-6}$ carbocyclyl substituted with 0-3 R$_e$, and —(CH$_2$)$_r$-heterocyclyl substituted with 0-3 R$_e$; or R$_6$ and R$_7$ together with the carbon atom to which they are both attached form a cycloalkyl substituted with 0-5 R$_e$; and R$_9$ is independently selected from F, Cl, Br, C$_{1-4}$alkyl, nitro, —(CHR)$_r$S(O)$_p$R$_c$, —(CHR)$_r$S(O)$_p$NR$_a$R$_a$, —(CHR)$_r$N-R$_a$S(O)$_p$R$_c$, —(CHR)$_r$OR$_b$, —(CHR)$_r$CN, —(CHR)$_r$ NR$_a$R$_a$, —(CHR)$_r$NR$_a$C(=O)R$_b$, —(CHR)$_r$NR$_a$C(=O) NR$_a$R$_a$, —(CHR)$_r$C(=O)OR$_b$, —(CHR)$_r$C(=O)R$_b$, —(CHR)$_r$ OC(=O)R$_b$, —(CHR)$_r$C(=O)NR$_a$R$_a$, —(CHR)$_r$-cycloalkyl, —(CHR)$_r$-heterocyclyl, —(CHR)$_r$-aryl, and —(CHR)$_r$-heteroaryl, wherein said alkyl, cycloalkyl, heterocyclyl, aryl, or heteroaryl is substituted with 0-4 R$_e$.

In another aspect, the present invention provides compounds of Formula (II) or stereoisomers, tautomers, pharmaceutically acceptable salts, solvates, or prodrugs thereof, wherein:

R$_3$ is independently selected from H, —OR$_b$, and —S(O)$_p$R$_c$;

R$_4$ is independently selected from H, F, Cl, Br, and C$_{1-4}$ alkyl substituted with 0-3 R$_e$;

$R_6$ and $R_7$ are independently selected from H, $C_{1-3}$ alkyl, —$(CH_2)_rOR_b$, —$NR_aR_a$, —$(CH_2)_rNR_aC(=O)OR_b$, —$(CH_2)$—$C_{3-6}$ carbocyclyl substituted with 0-3 $R_e$, and —$(CH_2)_r$-heterocyclyl substituted with 0-3 $R_e$;

$R_9$ is independently selected from F, Cl, Br, $C_{1-4}$ alkyl, $S(O)_pR_c$, —$OR_b$, —$(CHR_d)_rC(=O)OR_b$, —$(CHR_d)_rC(=O)R_b$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)$—$C_{3-10}$carbocyclyl substituted with 0-5 $R_e$, and —$(CH_2)_r$-heterocyclyl substituted with 0-5 $R_e$;

$R_c$, at each occurrence, is independently selected from $C_{1-6}$ alkyl substituted with 0-5 $R_e$, $C_{2-6}$alkenyl substituted with 0-5 $R_e$, $C_{2-6}$alkynyl substituted with 0-5 $R_e$, $C_{3-6}$carbocyclyl, and heterocyclyl;

$R_d$, at each occurrence, is independently selected from H and $C_{1-4}$alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, $NO_2$, =O, $CO_2H$, —$(CH_2)_rOC_{1-5}$ alkyl, —$(CH_2)_rOR_f$, $S(O)_pR_f$, and —$(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl; and r, at each occurrence, is independently selected from zero, 1, 2, 3, and 4;

other variables are as defined in Formula (I) above.

In another aspect, the present invention provides compounds of Formula (III):

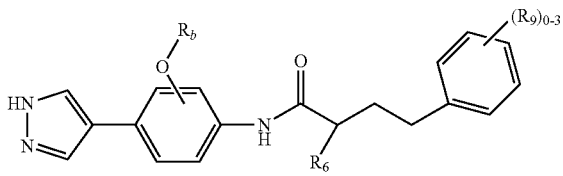

(III)

or stereoisomers, tautomers, pharmaceutically acceptable salts, solvates, or prodrugs thereof, wherein:

$R_6$ is independently selected from H, $C_{1-4}$alkyl substituted with 0-4 $R_e$, and $NR_aR_a$;

$R_9$ is independently selected from F, Cl, Br, and $C_{1-4}$ alkyl substituted with 0-4 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —$(CH_2)_r$—$C_{3-10}$carbocyclyl substituted with 0-5 $R_e$, and —$(CH_2)_r$-heterocyclyl substituted with 0-5 $R_e$;

$R_b$, at each occurrence, is independently selected from H and $C_{1-6}$ alkyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, $NO_2$, =O, $CO_2H$, —$(CH_2)_rOC_{1-5}$ alkyl, —$(CH_2)_rOR_f$, $S(O)_pR_f$, $S(O)_pNR_fR_f$, and —$(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

In another aspect, the present invention provides compounds of Formula (IV):

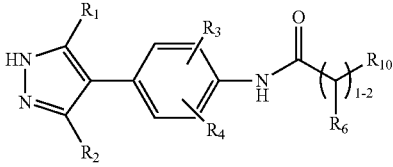

(IV)

or stereoisomers, tautomers, pharmaceutically acceptable salts, solvates, or prodrugs thereof, wherein:

$R_1$ is independently selected from H, F, Cl, Br, OH, CN, $NR_aR_a$, and $C_{1-4}$ alkyl substituted with 0-3 $R_e$;

$R_2$ is independently selected from H, —$(CH_2)_rOR_b$, $(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rCN$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_pNR_aR_a$, —$(CH_2)_r$—$C_{3-6}$ carbocyclyl substituted with 0-3 $R_e$, and —$(CH_2)_r$-heterocyclyl substituted with 0-3 $R_e$;

$R_3$ is independently selected from H, —$OR_b$, and —$S(O)_pR_c$;

$R_4$ is independently selected from H, F, Cl, Br, and $C_{1-4}$ alkyl substituted with 0-3 $R_e$;

$R_6$ is independently selected from H and $C_{1-4}$alkyl; alternatively, two adjacent $R_6$ groups may also form a cycloalkyl substituted with 0-5 $R_e$ when n is 2;

$R_{10}$ is independently selected from $NR_{11}R_{12}$ and phenyl substituted with 0-5 $R_9$;

$R_9$ is independently selected from F, Cl, Br, $C_{1-4}$ alkyl, —$(CHR)_rS(O)_pR_c$, —$(CHR_d)_rS(O)_pNR_aR_a$, —$(CHR_d)_rNR_aS(O)_pR_c$, —$(CHR_d)_rOR_b$, —$(CHR_d)_rCN$, —$(CHR_d)_rNR_aR_a$, —$(CHR_d)_rNR_aC(=O)R_b$, —$(CHR_d)_rC(=O)OR_b$, —$(CHR_d)_rC(=O)R_b$, —$(CHR_d)_r$ $OC(=O)R_b$, —$(CHR_d)_rC(=O)NR_aR_a$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$;

$R_{11}$ and $R_{12}$ together with the nitrogen atom to which they are both attached form a heterocyclic ring substituted with 0-5 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5

$R_e$, —(CH$_2$)$_r$—C$_{3-10}$carbocyclyl substituted with 0-5 $R_e$, and —(CH$_2$)$_r$-heterocyclyl substituted with 0-5 $R_e$; or $R_a$ and $R_a$ together with the nitrogen atom to which they are both attached form a heterocyclic ring substituted with 0-5 $R_e$;

$R_b$, at each occurrence, is independently selected from H, C$_{1-6}$ alkyl substituted with 0-5 $R_e$, C$_{2-6}$ alkenyl substituted with 0-5 $R_e$, C$_{2-6}$ alkynyl substituted with 0-5 $R_e$, —(CH$_2$)$_r$—C$_{3-10}$carbocyclyl substituted with 0-5 $R_e$, and —(CH$_2$)$_r$-heterocyclyl substituted with 0-5 $R_e$;

$R_c$, at each occurrence, is independently selected from C$_{1-6}$ alkyl substituted with 0-5 $R_e$, C$_{2-6}$alkenyl substituted with 0-5 $R_e$, C$_{2-6}$alkynyl substituted with 0-5 $R_e$, C$_{3-6}$carbocyclyl, and heterocyclyl;

$R_d$, at each occurrence, is independently selected from H and C$_{1-4}$alkyl substituted with 0-5 $R_e$;

$R_e$, at each occurrence, is independently selected from C$_{1-6}$ alkyl substituted with 0-5 $R_f$, C$_{2-6}$ alkenyl, C$_{2-6}$ alkynyl, —(CH$_2$)$_r$—C$_{3-6}$ cycloalkyl, F, Cl, Br, CN, NO$_2$, =O, CO$_2$H, —(CH$_2$)$_r$OC$_{1-5}$ alkyl, —(CH$_2$)$_r$OR$_f$, S(O)$_p$R$_f$, S(O)$_p$NR$_f$R$_f$, and —(CH$_2$)$_r$NR$_f$R$_f$;

$R_f$, at each occurrence, is independently selected from H, C$_{1-5}$ alkyl, C$_{3-6}$ cycloalkyl, and phenyl, or $R_f$ and $R_f$ together with the nitrogen atom to which they are both attached form a heterocyclic ring optionally substituted with C$_{1-4}$alkyl;

p, at each occurrence, is independently selected from zero, 1, and 2; and r, at each occurrence, is independently selected from zero, 1, 2, 3, and 4.

In another aspect, the present invention provides compounds of Formula (V):

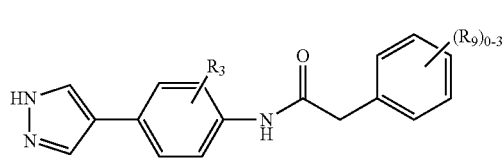

(V)

or stereoisomers, tautomers, pharmaceutically acceptable salts, solvates, or prodrugs thereof, wherein:
$R_3$ is —OR$_b$;
$R_9$ is independently selected from F, Cl, Br, C$_{1-4}$ alkyl substituted with 0-4 $R_e$;
$R_b$, at each occurrence, is independently selected from H, C$_{1-6}$ alkyl substituted with 0-5 $R_e$, —(CH$_2$)$_r$—C$_{3-10}$carbocyclyl substituted with 0-5 $R_e$, and —(CH$_2$)$_r$-heterocyclyl substituted with 0-5 $R_e$;
$R_e$, at each occurrence, is independently selected from C$_{1-6}$ alkyl substituted with 0-5 $R_f$, C$_{2-6}$ alkenyl, C$_{2-6}$ alkynyl, —(CH$_2$)$_r$—C$_{3-6}$ cycloalkyl, F, Cl, Br, CN, NO$_2$, =O, CO$_2$H, —(CH$_2$)$_r$OC$_{1-5}$ alkyl, —(CH$_2$)$_r$OR$_f$, S(O)$_p$R$_f$, S(O)$_p$NR$_f$R$_f$, and —(CH$_2$)$_r$NR$_f$R$_f$;
$R_f$, at each occurrence, is independently selected from H, C$_{1-5}$ alkyl, C$_{3-6}$ cycloalkyl, and phenyl, or $R_f$ and $R_f$ together with the nitrogen atom to which they are both attached form a heterocyclic ring optionally substituted with C$_{1-4}$alkyl;
p, at each occurrence, is independently selected from zero, 1, and 2; and
r, at each occurrence, is independently selected from zero, 1, 2, 3, and 4.

In another aspect, the present invention provides compounds of Formula (VI):

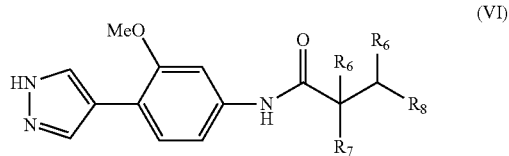

(VI)

or stereoisomers, tautomers, pharmaceutically acceptable salts, solvates, or prodrugs thereof, wherein:
$R_6$ is H or two adjacent $R_6$ groups form a cycloalkyl;
$R_7$ is independently selected from NH$_2$ or OH;
$R_8$, is independently selected from

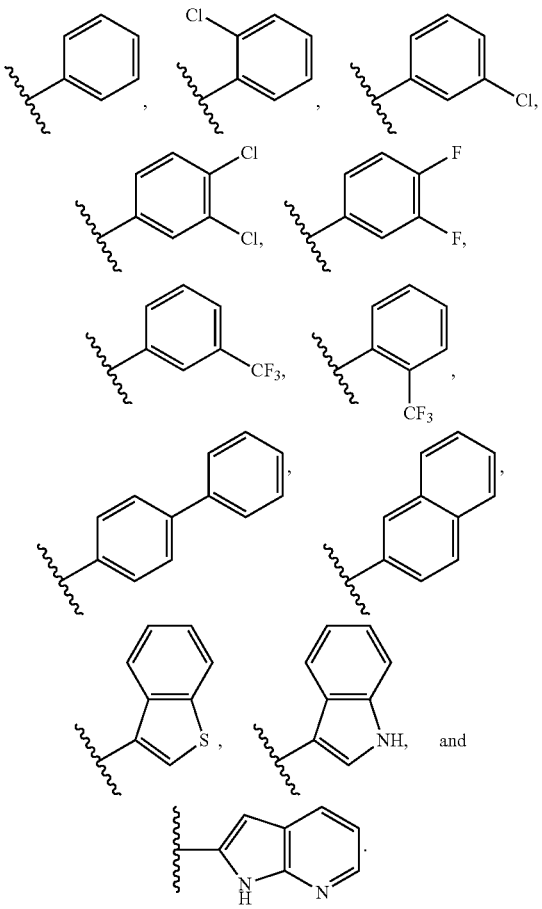

In one embodiment, the present invention provides compounds of Formula (I), or stereoisomers, tautomers, pharmaceutically acceptable salts, solvates, or prodrugs thereof, wherein:
$R_1$ is independently H, F, Cl, Br, NR$_a$R$_a$, or C$_{1-4}$alkyl;
$R_2$ is H, —(CH$_2$)$_r$OR$_b$, (CH$_2$)$_r$S(O)$_p$R$_c$, —(CH$_2$)$_r$C(=O)R$_b$, —(CH$_2$)$_r$NR$_a$R$_a$, —(CH$_2$)$_r$C(=O)NR$_a$R$_a$, —(CH$_2$)$_r$CN, —(CH$_2$)$_r$NR$_a$C(=O)R$_b$, —(CH$_2$)$_r$NR$_a$C(=O)OR$_b$, —(CH$_2$)$_r$OC(=O)NR$_a$R$_a$, —(CH$_2$)$_r$NR$_a$C(=O)NR$_a$R$_a$, —(CH$_2$)$_r$C(=O)OR$_b$, —(CH$_2$)$_r$S(O)$_p$NR$_a$R$_a$, C$_{1-4}$ alkyl substituted with 0-3 $R_e$ —(CH$_2$)$_r$—C$_{3-6}$ carbocyclyl substituted with 0-3 $R_e$, and —(CH$_2$)$_r$-heterocyclyl substituted with 0-3 $R_e$;

$R_3$ is H, —$(CH_2)_rOR_b$, $(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rC(=O)(CH_2)_rNR_aR_a$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, or —$(CH_2)_r$-heterocyclyl substituted with 0-3 $R_e$;

$R_4$ is H, F, Cl, Br, OH, $OC_{1-4}$ alkyl, and $C_{1-4}$ alkyl;

$R_5$ is H or $C_{1-4}$ alkyl;

$R_6$ and $R_7$ are independently selected from H, $C_{1-4}$alkyl substituted with 0-4 $R_e$, —$(CH_2)_rOR_b$, —$(CH_2)_rS(O)_pR_c$, —$(CH_2)_rC(=O)R_b$, —$(CH_2)_rNR_aR_a$, —$(CH_2)_rC(=O)NR_aR_a$, —$(CH_2)_rC(=O)(CH_2)_rNR_aR_a$, —$(CH_2)_rNR_aC(=O)R_b$, —$(CH_2)_rNR_aC(=O)OR_b$, —$(CH_2)_rOC(=O)NR_aR_a$, —$(CH_2)_rNR_aC(=O)NR_aR_a$, —$(CH_2)_rC(=O)OR_b$, —$(CH_2)_rS(O)_pNR_aR_a$, —$(CH_2)_rNR_aS(O)_pNR_aR_a$, —$(CH_2)_rNR_aS(O)_pR_c$, $(CH_2)_r$—$C_{3-6}$ carbocyclyl substituted with 0-3 $R_e$, and —$(CH_2)_r$-heterocyclyl substituted with 0-3 $R_e$, or $R_6$ and $R_7$ together with the carbon atom to which they are both attached form a cycloalkyl substituted with 0-5 Re; or, two adjacent $R_6$ groups form a cycloalkyl substituted with 0-5 $R_e$;

$R_8$ is aryl or heteroaryl, each substituted with 0-5 $R_9$;

$R_9$ is F, Cl, Br, $C_{1-4}$alkyl, $C_{2-4}$alkenyl, $C_{2-4}$alkynyl, nitro, —$(CHR_d)_rS(O)_pR_c$, —$(CHR_d)_rS(O)_pNR_aR_a$, —$(CHR_d)_rNR_aS(O)_pR_c$, —$(CHR_d)_rOR_b$, —$(CHR_d)_rCN$, —$(CHR_d)_rNR_aR_a$, —$(CHR_d)_rNR_aC(=O)R_b$, —$(CHR_d)_rNR_aC(=O)NR_aR_a$, —$(CHR_d)_rC(=O)OR_b$, —$(CHR_d)_rC(=O)R_b$, —$(CHR_d)_r$ $OC(=O)R_b$, —$(CHR_d)_rC(=O)NR_aR_a$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$; and alternatively, two adjacent $R_9$ groups are combined to form a carbocyclic or heterocyclic ring comprising carbon atoms and 1-3 hetero atoms selected from N, O, and $S(O)_p$, wherein the carbocyclic and heterocyclic rings are substituted with 0-4 $R_e$.

In another embodiment, the present invention provides compounds of Formula (I), or stereoisomers, tautomers, pharmaceutically acceptable salts, solvates, or prodrugs thereof, wherein:

$R_1$ is H or $C_{1-4}$alkyl;

$R_2$ is H or $C_{1-4}$alkyl;

$R_3$ is —$(CH_2)_rOR_b$, $(CH_2)_rS(O)_pR_c$;

$R_4$ is H, F, Cl, Br, OH, and $C_{1-4}$ alkyl;

$R_5$ is H;

$R_6$ and $R_7$ are independently selected from H, $C_{1-4}$alkyl substituted with 0-4 $R_e$, $OR_b$, —$NR_aR_a$, —$NR_aC(=O)R_b$, —$(CH_2)_rNR_aS(O)_pR_c$, or $R_6$ and $R_7$ together with the carbon atom to which they are both attached form a cycloalkyl substituted with 0-5 $R_e$;

$R_8$ is aryl substituted with 0-5 $R_9$; and $R_9$ is F, Cl, Br, $C_{1-4}$alkyl, $C_{2-4}$alkenyl, $C_{2-4}$alkynyl, nitro, —$(CHR_d)_rS(O)_pR_c$, —$(CHR_d)_rS(O)_pNR_aR_a$, —$(CHR_d)_rNR_aS(O)_pR_c$, —$(CHR_d)_rOR_b$, —$(CHR_d)_rCN$, —$(CHR_d)_rNR_aR_a$, —$(CHR_d)_rNR_aC(=O)R_b$, —$(CHR_d)_rNR_aC(=O)NR_aR_a$, —$(CHR_d)_rC(=O)OR_b$, —$(CHR_d)_rC(=O)R_b$, —$(CHR_d)_r$ $OC(=O)R_b$, —$(CHR_d)_rC(=O)NR_aR_a$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$.

In another embodiment, the present invention provides compounds of Formula (II), or stereoisomers, tautomers, pharmaceutically acceptable salts, solvates, or prodrugs thereof, wherein:

$R_1$ is H or $C_{1-4}$alkyl;

$R_2$ is H or $C_{1-4}$alkyl;

$R_3$ is H, —$(CH_2)_rOR_b$, $(CH_2)_rS(O)_pR_c$;

$R_4$ is H, F, Cl, Br, OH, and $C_{1-4}$ alkyl;

$R_5$ is H;

$R_6$ and $R_7$ are independently selected from H, $C_{1-4}$alkyl substituted with 0-4 $R_e$, $OR_b$, —$NR_aR_a$, —$NR_aC(=O)R_b$, —$(CH_2)_rNR_aS(O)_pR_c$, or $R_6$ and $R_7$ together with the carbon atom to which they are both attached form a cycloalkyl substituted with 0-5 $R_e$; and $R_9$ is F, Cl, Br, $C_{1-4}$alkyl, $C_{2-4}$alkenyl, $C_{2-4}$alkynyl, nitro, —$(CHR_d)_rS(O)_pR_c$, —$(CHR_d)_rS(O)_pNR_aR_a$, —$(CHR_d)_rNR_aS(O)_pR_c$, —$(CHR_d)_rOR_b$, —$(CHR_d)_rCN$, —$(CHR_d)_rNR_aR_a$, —$(CHR_d)_rNR_aC(=O)R_b$, —$(CHR_d)_rNR_aC(=O)NR_aR_a$, —$(CHR_d)_rC(=O)OR_b$, —$(CHR_d)_rC(=O)R_b$, —$(CHR_d)_r$ $OC(=O)R_b$, —$(CHR_d)_rC(=O)NR_aR_a$, —$(CHR_d)_r$-cycloalkyl, —$(CHR_d)_r$-heterocyclyl, —$(CHR_d)_r$-aryl, and —$(CHR_d)_r$-heteroaryl, wherein said alkyl, cycloalkyl, heterocyclyl, aryl, or heteroaryl is substituted with 0-4 $R_e$.

In another aspect, the present invention provides a compound selected from any subset list of compounds exemplified in the present application.

In another embodiment, the compounds of the present invention have ROCK $IC_{50}$ values $\leq 10$ µM.

In another embodiment, the compounds of the present invention have ROCK $IC_{50}$ values $\leq 1$ µM.

In another embodiment, the compounds of the present invention have ROCK $IC_{50}$ values $\leq 0.1$ µM.

In another embodiment, the compounds of the present invention have ROCK $IC_{50}$ values $\leq 0.05$ µM.

In another embodiment, the compounds of the present invention have ROCK $IC_{50}$ values $\leq 0.01$ µM.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate, thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s).

In another embodiment, the present invention provides a method for the treatment and/or prophylaxis of a condition associated with aberrant ROCK activity comprising administering to a patient in need of such treatment and/or prophylaxis a therapeutically effective amount of at least one of the compounds of the present invention or a stereoisomer, a tautomer, a pharmaceutically acceptable salt, or a solvate thereof. As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" cover the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a patient that has not yet presented with a clinical disease state, whereas secondary prevention is defined as preventing a second occurrence of the same or similar clinical disease state. In another embodiment, the present invention provides a combined preparation of a compound of the present invention and additional therapeutic agent(s) for simultaneous, separate or sequential use in therapy.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and iso-propoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro (F), chloro (Cl), bromo (Br), and iodo (I). "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle", "carbocyclyl" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocyclyl" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocyclyl" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle", "heterocyclyl", or "heterocyclic ring" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs,* Elsevier (1985), and Widder, K. et al., eds., *Methods in Enzymology,* 112:309-396, Academic Press (1985);

b) Bundgaard, H., Chapter 5, "Design and Application of Prodrugs", Krosgaard-Larsen, P. et al., eds., *A Textbook of Drug Design and Development,* pp. 113-191, Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988); and e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice,* The Royal Society of Chemistry, Cambridge, UK (1994); Testa, B. et al., *Hydrolysis in Drug and Prodrug Metabolism. Chemistry, Biochemistry and Enzymology,* VCHA and Wiley-VCH, Zurich, Switzerland (2003); Wermuth, C. G., ed., *The Practice of Medicinal Chemistry,* Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2$H" or "D". The term "deuterated" herein, by itself or used to modify a compound or group, refers to replacement of one or more hydrogen atom(s), which is attached to carbon(s), with a deuterium atom. Isotopes of carbon include $^{13}$C and $^{14}$C.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "saturated" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me Methyl
Et Ethyl
Pr Propyl
i-Pr Isopropyl
Bu Butyl
i-Bu Isobutyl
t-Bu tert-butyl
Ph Phenyl
Bn Benzyl
Boc tert-butyloxycarbonyl
AcOH or HOAc acetic acid
$AlCl_3$ aluminum chloride
AIBN Azobisisobutyronitrile
$BBr_3$ boron tribromide
$BCl_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonyl-methanimidate
CBz Carbobenzyloxy
$CH_2Cl_2$ Dichloromethane
$CH_3CN$ or ACN Acetonitrile
$CDCl_3$ deutero-chloroform
$CHCl_3$ Chloroform
mCPBA or m-CPBA meta-chloroperbenzoic acid
$Cs_2CO_3$ cesium carbonate
$Cu(OAc)_2$ copper (II) acetate
$Cy_2NMe$ N-cyclohexyl-N-methylcyclohexanamine
DBU 1,8-diazabicyclo[5.4.0]undec-7-ene
DCE 1,2 dichloroethane
DCM dichloromethane
DEA diethylamine
Dess-Martin 1,1,1-tris(acetyloxy)-1,1-dihydro-1,2-beniziodoxol-3-(1H)-one
DIC or DIPCDI diisopropylcarbodiimide
DIEA, DIPEA or diisopropylethylamine Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylpholano)benzene
EDC N-(3-dimthylaminopropyl)-N'-ethylcarbodiimide
EDCI N-(3-dimthylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
$Et_3N$ or TEA triethylamine
EtOAc ethyl acetate
$Et_2O$ diethyl ether
EtOH Ethanol
GMF glass microfiber filter
Grubbs (II) (1,3-bis(2,4,6-trimethylphenyl)-2-imidazolidinylidene)dichloro (phenylmethylene)(triycyclohexylphosphine)ruthenium
HCl hydrochloric acid
HATU O-(7-azabenzotriazol-1-yl)-N,N,N',N'-tetramethyl-uronium hexafluorophosphate
HEPES 4-(2-hydroxyethyl)piperaxine-1-ethanesulfonic acid
Hex Hexane
HOBt or HOBT 1-hydroxybenzotriazole
$H_2SO_4$ sulfuric acid
$K_2CO_3$ potassium carbonate
KOAc potassium acetate
$K_3PO_4$ potassium phosphate
LAH lithium aluminum hydride
LG leaving group
LiOH lithium hydroxide
MeOH Methanol
$MgSO_4$ magnesium sulfate
MsOH or MSA methylsulfonic acid
NaCl sodium chloride
NaH sodium hydride
$NaHCO_3$ sodium bicarbonate
$Na_2CO_3$ sodium carbonate
NaOH sodium hydroxide
$Na_2SO_3$ sodium sulfite
$Na_2SO_4$ sodium sulfate
NBS N-bromosuccinimide
NCS N-chlorosuccinimide
$NH_3$ Ammonia
$NH_4Cl$ ammonium chloride
$NH_4OH$ ammonium hydroxide
OTf triflate or trifluoromethanesulfonate
$Pd_2(dba)_3$ tris(dibenzylideneacetone)dipalladium(0)
$Pd(OAc)_2$ palladium(II) acetate
Pd/C palladium on carbon
$Pd(dppf)Cl_2$ [1,1'-bis(diphenylphosphino)-ferrocene]dichloropalladium(II)
$Ph_3PCl_2$ triphenylphosphine dichloride
PG protecting group
$POCl_3$ phosphorus oxychloride
i-PrOH or IPA isopropanol
PS polystyrene
SEM-Cl 2-(trimethysilyl)ethoxymethyl chloride
$SiO_2$ silica oxide
$SnCl_2$ tin(II) chloride
TBAI tetra-n-butylammonium iodide
TEA triethylamine
TFA trifluoroacetic acid
THF tetrahydrofuran TMSCHN$_2$ trimethylsilyldiazomethane
T$_3$P propane phosphonic acid anhydride
TRIS tris (hydroxymethyl) aminomethane The compounds of the present invention can be prepared in a number of ways known to one skilled in the art of organic synthesis.

IV. Biology

In Vitro Assays

The effectiveness of compounds of the present invention as ROCK inhibitors can be determined in a 30 μL assay containing 20 mM HEPES, pH 7.5, 20 mM MgCl$_2$, 0.015% Brij-35, 4 mM DTT, 5 μM ATP and 1.5 μM peptide substrate (FITC-AHA-AKRRRLSSLRA-OH). Compounds were dissolved in DMSO so that the final concentration of DMSO was <2%, and the reaction was initiated with Rho kinase variants. After incubation, the reaction was terminated by the addition of EDTA and the phosphorylated and non-phosphorylated peptides separated using a LABCHIP® 3000 Reader (Caliper Life Sciences). Controls consisted of assays that did not contain compound, and backgrounds consisted of assays that contained enzyme and substrate but had EDTA from the beginning of the reaction to inhibit kinase activity. Compounds were tested in dose-response format, and the inhibition of kinase activity was calculated at each concentration of compound. The inhibition data were fit using a curve-fitting program to determine the IC$_{50}$; i.e., the concentration of compound required to inhibit 50% of kinase activity.

Representative Examples were tested in the ROCK assay described above and found having ROCK inhibitory activity. A range of ROCK inhibitory activity (IC$_{50}$ values) of ≤50 μM (50000 nM) was observed. Table A below lists the ROCK IC$_{50}$ values measured for the following examples.

TABLE A

| Example No. | ROCK1 IC$_{50}$ (nM) | ROCK2 IC$_{50}$ (nM) |
| --- | --- | --- |
| 1 | 7.07 | 2.54 |
| 3 | 27.33 | 3.96 |
| 5 | 10.15 | 5.00 |
| 6 | 8.78 | 3.25 |
| 8 | 10.24 | 8.02 |
| 9 | 31.64 | 17.89 |
| 11 | 50.00 | 14.26 |
| 12 | 19.91 | 23.55 |
| 13 | 68.39 | 10.32 |
| 14 | 12.58 | 13.37 |
| 18 | 122.80 | 11.12 |
| 19 | 13.92 | 37.46 |
| 20 | 20.97 | 7.02 |
| 23 | 111.10 | 8.51 |
| 27 | 874.00 | 342.50 |
| 28 | 42.54 | 17.84 |
| 29 | 19.61 | 4.06 |
| 30 | 231.80 | 167.00 |

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the patient to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously). When administered intra-venous or intra-arterial, the dose can be given continuously or intermittent. Furthermore, formulation can be developed for intramuscularly and subcutaneous delivery that ensure a gradual release of the active pharmaceutical ingredient.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the inhibition of ROCK. Such compounds may be provided in a commercial kit, for example, for use in pharmaceutical research involving ROCK. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular and/or inflammatory disorder (as defined previously). In another embodiment, the package insert states that the pharmaceutical composition can be used in combination (as defined previously) with a second therapeutic agent to treat cardiovascular and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by many methods available to those skilled in the art of organic chemistry (Maffrand, J. P. et al., *Heterocycles*, 16(1):35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, 4th Edition, Wiley-Interscience (2006)).

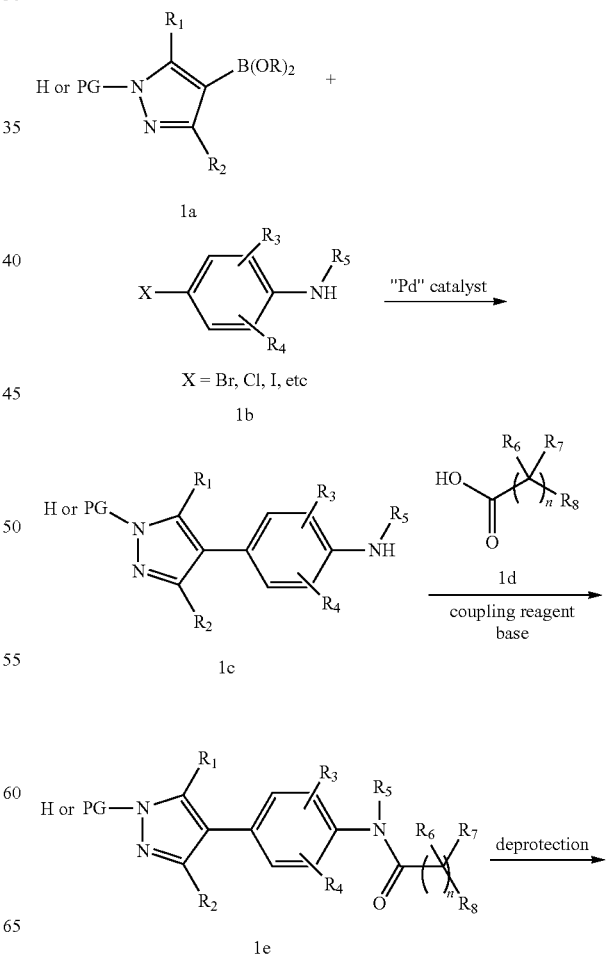

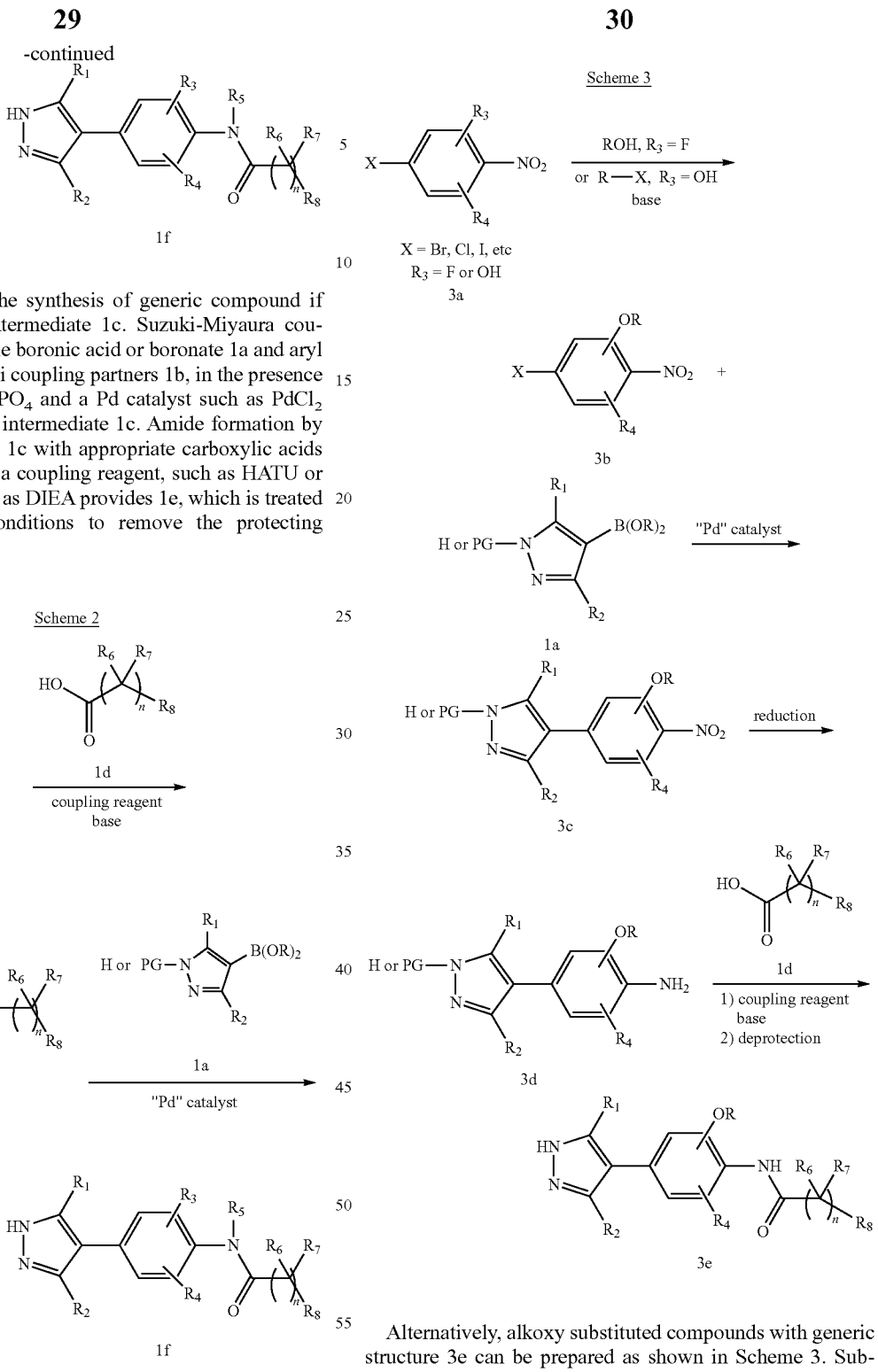

Scheme 1 shows the synthesis of generic compound 1f from the common intermediate 1c. Suzuki-Miyaura coupling between pyrazole boronic acid or boronate 1a and aryl halide, or other Suzuki coupling partners 1b, in the presence of a base such as $K_3PO_4$ and a Pd catalyst such as $PdCl_2$(dppf) affords aniline intermediate 1c. Amide formation by coupling intermediate 1c with appropriate carboxylic acids 1d in the presence of a coupling reagent, such as HATU or EDC, and a base such as DIEA provides 1e, which is treated under appropriate conditions to remove the protecting groups to afford 1f.

Alternatively, compounds with generic structure 1f can be prepared as shown in Scheme 2. Amide formation between substituted aniline derivatives 1b with appropriate carboxylic acids 1d affords 2a under conditions such as using HATU or EDC as a coupling reagent with a base such as DIEA or TEA. Suzuki-Miyaura coupling between 2a and boronic acid derivatives 1a in the presence of a base such as $K_3PO_4$ and a catalyst such as $PdCl_2$(dppf) affords target compounds 1f.

Alternatively, alkoxy substituted compounds with generic structure 3e can be prepared as shown in Scheme 3. Substitution of aryl fluoride 3a ($R_3$=F) with alcohols, or alkylation of phenol derivatives 3a ($R_3$=OH) with appropriate alkyl halides in the presence of a base such as NaH or $K_2CO_3$ affords 3b. Suzuki-Miyaura coupling between 3b and pyrazole boronic acid derivatives 1a using a base such as $K_3PO_4$ and a catalyst such as $PdCl_2$(dppf) affords 3c. The nitro group in 3c is reduced by either using a reducing reagent such as zinc or $SnCl_2$, or by hydrogenation to give the common intermediate 3d. Amide formation between 3d and the appropriate carboxylic acids 1d under conditions such as using HATU or EDC as a coupling reagent with a base such as DIEA or TEA, followed by removal of protecting group(s) affords 3e.

Purification of intermediates and final products was carried out via either normal or reverse phase chromatography. Normal phase chromatography was carried out using prepacked SiO$_2$ cartridges eluting with either gradients of hexanes and EtOAc or DCM and MeOH unless otherwise indicated. Reverse phase preparative HPLC was carried out using C18 columns eluting with gradients of Solvent A (90% H$_2$O, 10% MeOH, 0.1% TFA) and Solvent B (10% H$_2$O, 90% MeOH, 0.1% TFA, UV 220 nm) or with gradients of Solvent A (90% H$_2$O, 10% ACN, 0.1% TFA) and Solvent B (10% H$_2$O, 90% ACN, 0.1% TFA, UV 220 nm) or with gradients of Solvent A (98% H$_2$O, 2% ACN, 0.05% TFA) and Solvent B (98% ACN, 2% H$_2$O, 0.05% TFA, UV 220 nm) (or) SunFire Prep C18 OBD 5μ 30×100 mm, 25 min gradient from 0-100% B. A=H$_2$O/ACN/TFA 90:10:0.1. B=ACN/H$_2$O/TFA 90:10:0.1 (or) Waters XBridge C18, 19×200 mm, 5-μm particles; Guard Column: Waters XBridge C18, 19×10 mm, 5-μm particles; Solvent A: water with 20-mM ammonium acetate; Solvent B: 95:5 acetonitrile:water with 20-mM ammonium acetate; Gradient: 25-65% B over 20 minutes, then a 5-minute hold at 100% B; Flow: 20 mL/min or with gradients of Solvent A (5:95 acetonitrile:water with 0.1% formic acid) and Solvent B (95:5 acetonitrile:water with 0.1% formic acid).

Unless otherwise stated, analysis of final products was carried out by reverse phase analytical HPLC.

Method A: SunFire C18 column (3.5 μm C18, 3.0×150 mm) Gradient elution (1.0 mL/min) from 10-100% Solvent B over 10 min and then 100% Solvent B for 5 min was used. Solvent A is (95% water, 5% acetonitrile, 0.05% TFA) and Solvent B is (5% water, 95% acetonitrile, 0.05% TFA, UV 254 nm).

Method B: XBridge Phenyl column (3.5 μm C18, 3.0×150 mm) Gradient elution (1.0 mL/min) from 10-100% Solvent B over 10 min and then 100% Solvent B for 5 min was used. Solvent A is (95% water, 5% acetonitrile, 0.05% TFA) and Solvent B is (5% water, 95% acetonitrile, 0.05% TFA, UV 254 nm).

Method C: Waters BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes; Flow: 1.11 mL/min.

Method D: Waters BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes; Flow: 1.11 mL/min.

INTERMEDIATE 1 tert-Butyl 4-(4-amino-2-methoxyphenyl)-1H-pyrazole-1-carboxylate

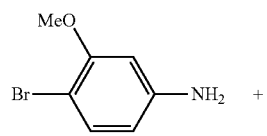

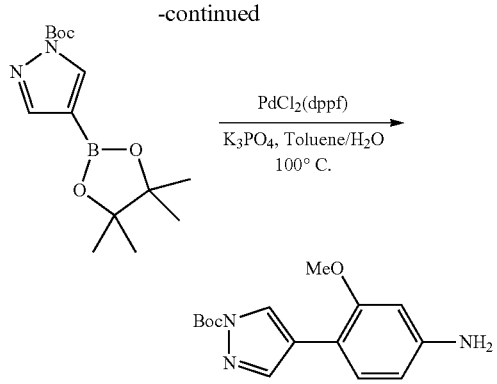

To a solution of 4-bromo-3-methoxyaniline (5.7 g, 28.2 mmol) in toluene (100 mL) and water (10 mL) were added tert-butyl 4-(4,4,5,5-tetramethyl-1,3,2-dioxaborolan-2-yl)-1H-pyrazole-1-carboxylate (9.96 g, 33.9 mmol), potassium phosphate (8.98 g, 42.3 mmol) and PdCl$_2$(dppf)-DCM (1.152 g, 1.411 mmol) at RT. The reaction was stirred under argon at 95° C. for 2.5 hrs and then was cooled to RT. The reaction mixture was diluted with EtOAc, washed with H$_2$O, saturated NaHCO$_3$ and brine. The organic phase was dried over sodium sulfate, filtered and concentrated. The crude product was purified by normal phase chromatography to give Intermediate 1 as light tan solid (5.1 g, 63% yield). LCMS (ESI) m/z: 290.1 (M+H)$^+$; $^1$H NMR (400 MHz, chloroform-d) δ 8.35 (d, J=0.5 Hz, 1H), 8.01 (s, 1H), 7.29 (d, J=8.0 Hz, 1H), 6.37-6.26 (m, 2H), 3.84 (s, 3H), 3.79 (br. s., 2H), 1.66 (s, 9H).

INTERMEDIATE 2

3-Methoxy-4-(1H-pyrazol-4-yl)aniline

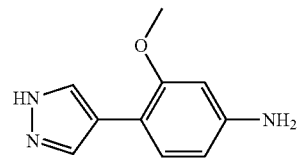

Intermediate 2 was synthesized by following a similar procedure to Intermediate 1, in which the Boc group was removed under the aqueous basic reaction condition. LCMS (ESI) m/z: 190.1 (M+H)$^+$.

INTERMEDIATE 3 tert-Butyl 4-(4-aminophenyl)-1H-pyrazole-1-carboxylate

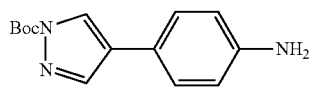 [SMILES: CC(C)(C)OC(=O)n1cc(-c2ccc(N)cc2)cn1]

Intermediate 3 was synthesized by following a similar procedure to Intermediate 1 by replacing 4-bromo-3-methoxyaniline with 4-bromoaniline. LCMS (ESI) m/z: 260.1 (M+H)$^+$; $^1$H NMR (400 MHz, chloroform-d) δ 8.18 (s, 1H), 7.96-7.91 (m, 1H), 7.33 (d, J=8.4 Hz, 2H), 6.83-6.65 (m, 2H), 3.76 (br. s., 2H), 1.35-1.22 (2s, 9H).

INTERMEDIATE 4

2-(2-(Dimethylamino)ethoxy)-4-(1H-pyrazol-4-yl) aniline

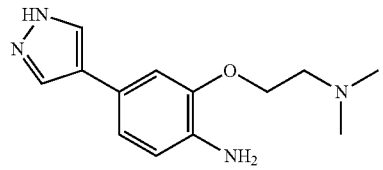 [SMILES: CN(C)CCOc1cc(-c2cn[nH]c2)ccc1N]

INTERMEDIATE 4A 2-(5-Bromo-2-nitrophenoxy)-N,N-dimethylethanamine

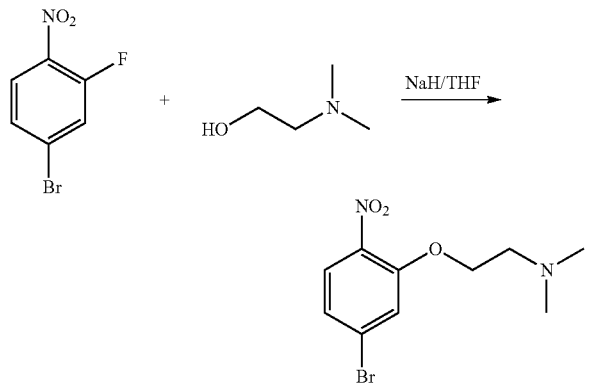

A flask charged with NaH (0.109 g, 2.73 mmol) was added THF (5 mL) followed by addition of 2-(dimethylamino)ethanol (0.251 mL, 2.500 mmol). After stirred at RT for 5 min, a solution of 4-bromo-2-fluoro-1-nitrobenzene (0.5 g, 2.273 mmol) dissolved in THF (5 mL) was added. The mixture was stirred at RT under argon overnight. Water was added carefully to quench the reaction. The reaction was partitioned between EtOAc and water. The aqueous layer was extracted with EtOAc. The combined organic solution was washed with brine, dried over Na₂SO₄, filtered and concentrated. The crude product was purified by normal phase chromatography to give Intermediate 4A as yellow oil (0.57 g, 87% yield). LCMS (ESI) m/z: 289.0/291.0 (M+H)⁺.

INTERMEDIATE 4B

N,N-Dimethyl-2-(2-nitro-5-(1H-pyrazol-4-yl)phenoxy)ethanamine

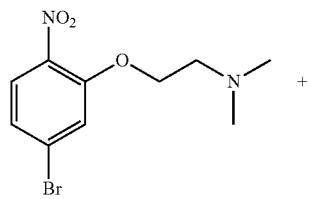

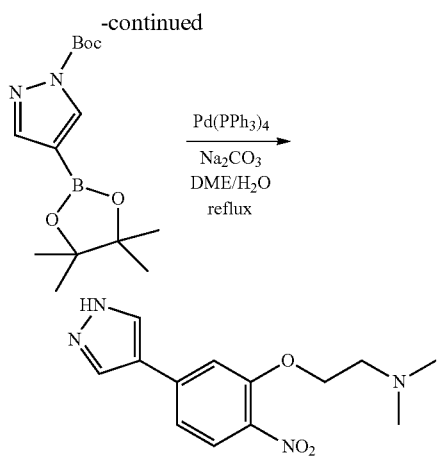

To a solution of Intermediate 4A (0.57 g, 1.97 mmol) in DME (10 mL) and water (2 mL) were added tert-butyl 4-(4,4,5,5-tetramethyl-1,3,2-dioxaborolan-2-yl)-1H-pyrazole-1-carboxylate (0.70 g, 2.40 mmol), Na₂CO₃ (0.42 g, 3.94 mmol) and Pd(Ph₃P)₄ (0.23 g, 0.20 mmol). The reaction was heated at reflux under argon for 2.5 hrs. It was then cooled and diluted with EtOAc, washed with water and brine, dried over Na₂SO₄, filtered and concentrated. Purification by normal phase chromatography afforded Intermediate 4B (0.25 g, 46% yield). LCMS (ESI) m/z: 277.1 (M+H)⁺.

INTERMEDIATE 4C, INTERMEDIATE 4

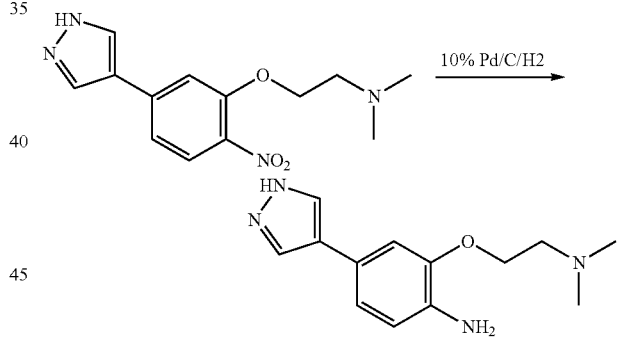

Intermediate 4B (0.25 g, 0.905 mmol) in MeOH was added catalytic amount of 10% Pd/C. The mixture was stirred under a hydrogen balloon for 20 hrs. It was filtered and solvent was removed to give Intermediate 4C as tan solid (0.20 g). LCMS (ESI) m/z: 247.2 (M+H)⁺.

INTERMEDIATE 5

4-(1H-Pyrazol-4-yl)-2-(2-(pyrrolidin-1-yl)ethoxy) aniline

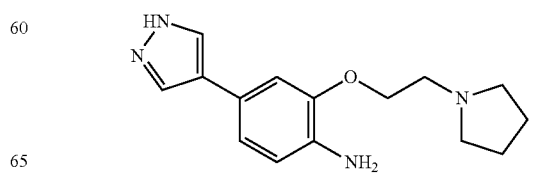

Intermediate 5 was prepared following a similar procedure as described in Intermediate 4 by replacing 2-(dimethylamino)ethanol with 2-(pyrrolidin-1-yl)ethanol in Intermediate 4A. LCMS (ESI) m/z: 273.2 (M+H)⁺.

EXAMPLE 1

(R)-2-Amino-N-(3-methoxy-4-(1H-pyrazol-4-yl)phenyl)-4-phenylbutanamide, TFA salt

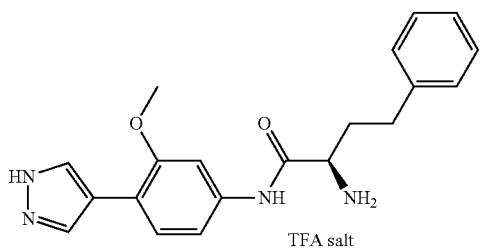 [SMILES: COc1cc(NC(=O)[C@H](N)CCc2ccccc2)ccc1-c1cn[nH]c1]

EXAMPLE 1A (R)-tert-Butyl 4-(4-(2-((tert-butoxycarbonyl)amino)-4-phenylbutanamido)-2-methoxyphenyl)-1H-pyrazole-1-carboxylate

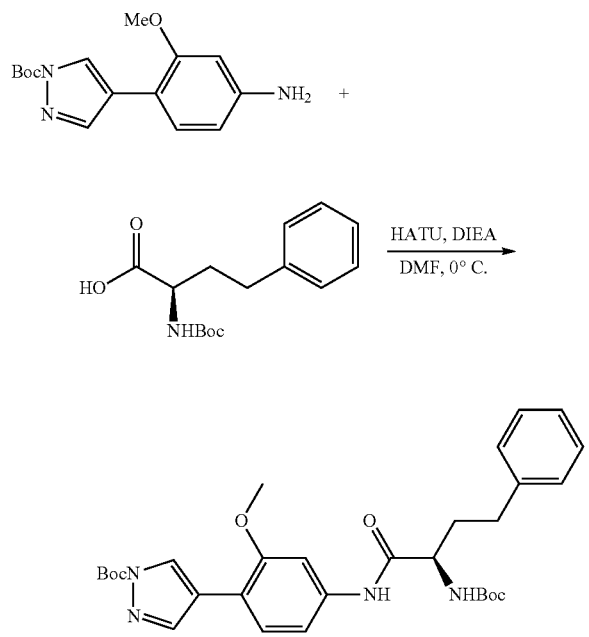

To a solution of Intermediate 1 (5.1 g, 17.63 mmol) in DMF (40 mL) were added (R)-2-((tert-butoxycarbonyl)amino)-4-phenylbutanoic acid (4.92 g, 17.63 mmol), DIEA (7.70 mL, 44.1 mmol), and HATU (7.04 g, 18.51 mmol) at 0° C. The reaction was stirred under argon at 0° C. for 2 hrs. The reaction mixture was diluted with EtOAc, washed with H₂O and brine. The organic phase was dried over sodium sulfate, filtered and concentrated. The crude product was purified by normal phase chromatography to afford 1A as white solid (9.9 g, 100%). LCMS (ESI) m/z: 551.2 (M+H)⁺. ¹H NMR (400 MHz, chloroform-d) δ 8.86 (br. s., 1H), 8.38 (s, 1H), 8.00 (s, 1H), 7.40 (br. s., 1H), 7.35 (d, J=8.3 Hz, 1H), 7.30-7.23 (m, 2H), 7.22-7.11 (m, 3H), 6.94 (dd, J=8.4, 1.9 Hz, 1H), 5.38 (d, J=8.0 Hz, 1H), 4.32 (d, J=3.8 Hz, 1H), 3.82 (s, 3H), 2.89-2.66 (m, 2H), 2.32-2.17 (m, 1H), 2.11-1.97 (m, 1H), 1.66 (s, 9H), 1.47 (s, 9H).

EXAMPLE 1B, EXAMPLE 1

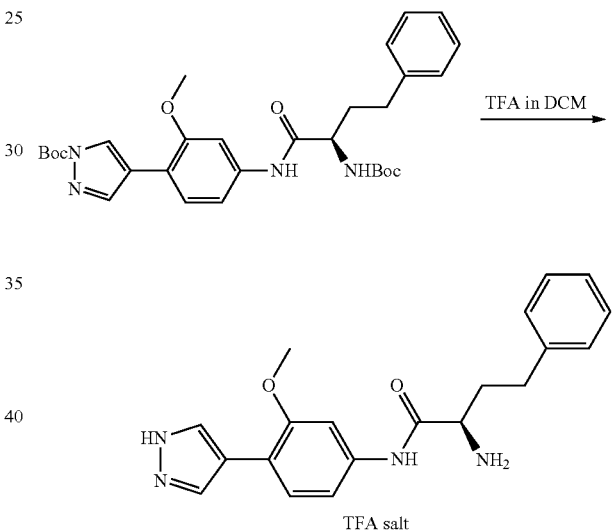

To a solution of Example 1A (3.32 g, 6.03 mmol) in DCM (25 mL) was added TFA (8 mL, 104 mmol) slowly at RT. The reaction was stirred under argon at RT for 1 hr. Solvent was removed. The crude product was purified by reverse phase chromatography to afford Example 1 as white solid (2.75 g, 98% yield). LCMS (ESI) m/z: 351.1 (M+H)⁺; ¹H NMR (500 MHz, methanol-d₄) δ 8.06 (s, 2H), 7.59 (d, J=8.3 Hz, 1H), 7.49 (d, J=2.2 Hz, 1H), 7.34-7.28 (m, 2H), 7.28-7.24 (m, 2H), 7.24-7.17 (m, 2H), 4.10 (t, J=6.5 Hz, 1H), 3.94 (s, 3H), 2.86-2.73 (m, 2H), 2.36-2.17 (m, 2H); Analytical HPLC RT=4.09 min (Method A), 4.78 min (Method B).

The following Examples in Table 1 were prepared by using a similar procedure as described in Example 1 by coupling Intermediate 1 or Intermediate 2 with the appropriate carboxylic acids in Example 1A. Various coupling reagents could be used other than the one described in Example 1 such as HATU, T₃P, BOP, PyBop, EDC/HOBt.

TABLE 1

| Ex. | R | Name | LCMS (M + H)+ | HPLC Method, RT (min.) | 1H NMR |
|---|---|---|---|---|---|
| 2 | 2-chlorophenyl group | 2-(2-chlorophenyl)-N-(3-methoxy-4-(1H-pyrazol-4-yl)phenyl)acetamide | 342.0 | A: 6.24 B: 6.79 | (400 MHz, DMSO-d$_6$) δ ppm 12.80 (1 H, d, J = 2.26 Hz), 10.24 (1 H, s), 8.05 (1 H, br. s.), 7.90 (1 H, br. s.), 7.54 (1 H, d, J = 8.28 Hz), 7.40-7.50 (3 H, m), 7.27-7.36 (2 H, m), 7.16 (1 H, dd, J = 8.28, 2.01 Hz), 3.78-3.89 (5 H, m) |
| 3 | (R)-2-amino-2-(2-chlorophenyl) group | (R)-2-amino-2-(2-chlorophenyl)-N-(3-methoxy-4-(1H-pyrazol-4-yl)phenyl)acetamide | 357.1 | A: 5.18 B: 6.51 | (400 MHz, DMSO-d$_6$) δ ppm 10.45 (1 H, s), 8.67 (3 H, br. s.), 7.93 (2 H, br. s.), 7.39-7.62 (5 H, m), 7.12-7.28 (2 H, m), 5.33 (1 H, br. s.), 3.77 (3 H, s) |
| 4 | (+/−)-1-(2-chlorophenyl)ethyl group | (+/−)-2-(2-chlorophenyl)-N-(3-methoxy-4-(1H-pyrazol-4-yl)phenyl)propanamide | 356.1 | A: 9.51 B: 10.09 | (400 MHz, DMSO-d$_6$) δ ppm 10.08 (1 H, s), 7.91 (2 H, d, J = 1.76 Hz), 7.36-7.50 (4 H, m), 7.19-7.31 (2 H, m), 7.14 (1 H, d, J = 8.28 Hz), 4.17 (1 H, br. s.), 3.76 (3 H, s), 1.39 (3 H, d, J = 7.03 Hz) |
| 5 | (R)-2-amino-3-(3,4-dichlorophenyl) group | (R)-2-amino-3-(3,4-dichlorophenyl)-N-(3-methoxy-4-(1H-pyrazol-4-yl)phenyl)propanamide | 405.0 | A: 5.72 B: 6.98 | (400 MHz, methanol-d$_4$) δ 8.04 (s, 2H), 7.55 (d, J = 8.3 Hz, 1H), 7.54-7.50 (m, 2H), 7.33 (d, J = 2.0 Hz, 1H), 7.24 (dd, J = 8.2, 2.1 Hz, 1H), 7.07 (dd, J = 8.3, 2.0 Hz, 1H), 4.18 (t, J = 7.3 Hz, 1H), 3.91 (s, 3H), 3.27 (d, J = 6.9 Hz, 1H), 3.17 (dd, J = 14.0, 7.6 Hz, 1H) |
| 6 | (R)-2-amino-3-(naphthalen-2-yl) group | (R)-2-amino-N-(3-methoxy-4-(1H-pyrazol-4-yl)phenyl)-3-(naphthalen-2-yl)propanamide | 387.1 | A: 5.59 B: 6.98 | (400 MHz, methanol-d$_4$) δ 8.03 (s, 2H), 7.91-7.78 (m, 4H), 7.53-7.47 (m, 3H), 7.45 (dd, J = 8.4, 1.7 Hz, 1H), 7.20 (d, J = 2.0 Hz, 1H), 7.04 (dd, J = 8.3, 2.0 Hz, 1H), 4.28 (t, J = 7.3 Hz, 1H), 3.82 (s, 3H), 3.47 (dd, J = 13.9, 6.9 Hz, 1H), 3.35 (dd, J = 8.8, 5.1 Hz, 1H) |
| 7 | (R)-2-amino-3-(1H-indol-3-yl) group | (R)-2-amino-3-(1H-indol-3-yl)-N-(3-methoxy-4-(1H-pyrazol-4-yl)phenyl)propanamide | 376.2 | A: 4.97 B: 6.08 | (400 MHz, methanol-d$_4$) δ 8.05 (s, 2H), 7.68 (d, J = 7.9 Hz, 1H), 7.55 (d, J = 8.3 Hz, 1H), 7.41 (d, J = 8.2 Hz, 1H), 7.29 (d, J = 2.0 Hz, 1H), 7.24 (s, 1H), 7.18-7.12 (m, 1H), 7.10-7.02 (m, 2H), 4.26 (t, J = 7.1 Hz, 1H), 3.89 (s, 3H), 3.51 (dd, J = 14.6, 6.6 Hz, 1H), 3.39 (dd, J = 14.7, 7.5 Hz, 1H) |
| 8 | (R)-2-amino-3-phenyl group | (R)-2-amino-N-(3-methoxy-4-(1H-pyrazol-4-yl)phenyl)-3-phenylpropanamide | 337.1 | A: 4.63 B: 5.72 | (400 MHz, methanol-d$_4$) δ 8.14 (s, 2H), 7.55 (d, J = 8.3 Hz, 1H), 7.41-7.27 (m, 6H), 7.07 (dd, J = 8.4, 2.0 Hz, 1H), 4.20 (t, J = 7.4 Hz, 1H), 3.91 (s, 3H), 3.28 (dd, J = 13.8, 7.1 Hz, 1H), 3.18 (dd, J = 13.8, 7.6 Hz, 1H) |

TABLE 1-continued

| Ex. | R | Name | LCMS (M + H)+ | HPLC Method, RT (min.) | 1H NMR |
|---|---|---|---|---|---|
| 9 | (S)-2-amino-3-(benzo[b]thiophen-3-yl) substituent | (S)-2-amino-3-(benzo[b]thiophen-3-yl)-N-(3-methoxy-4-(1H-pyrazol-4-yl)phenyl)propanamide | 393.1 | A: 8.20  B: 10.39 | (400 MHz, methanol-d4) δ 8.01 (s, 2H), 7.96-7.89 (m, 2H), 7.54-7.47 (m, 2H), 7.43-7.35 (m, 2H), 7.21 (d, J = 2.0 Hz, 1H), 6.99 (dd, J = 8.3, 2.0 Hz, 1H), 4.28 (t, J = 7.4 Hz, 1H), 3.86 (s, 3H), 3.58 (ddd, J = 14.5, 7.6, 0.4 Hz, 1H), 3.48 (dd, J = 14.5, 7.3 Hz, 1H) |
| 10 | 7-azaindol-2-ylmethyl amine substituent | (+/−)-2-amino-N-(3-methoxy-4-(1H-pyrazol-4-yl)phenyl)-3-(1H-pyrrolo[2,3-b]pyridin-2-yl)propanamide | 337.1 | A: 3.43  B: 4.19 | (400 MHz, methanol-d4) δ 8.28 (dd, J = 4.5, 1.3 Hz, 1H), 8.26 (s, 1H), 8.02 (s, 2H), 7.52 (d, J = 8.3 Hz, 1H), 7.49 (s, 1H), 7.29 (d, J = 2.0 Hz, 1H), 7.22 (dd, J = 7.7, 5.4 Hz, 1H), 7.03 (dd, J = 8.3, 2.0 Hz, 1H), 4.24 (t, J = 7.0 Hz, 1H), 3.88 (s, 3H), 3.54-3.48 (m, 1H), 3.42 (dd, J = 15.0, 7.1 Hz, 1H) |
| 11 | (R)-3-trifluoromethylphenyl substituent | (R)-2-amino-N-(3-methoxy-4-(1H-pyrazol-4-yl)phenyl)-3-(3-(trifluoromethyl)phenyl)propanamide | 405.1 | A: 6.74  B: 7.45 | (400 MHz, methanol-d4) δ 8.05 (s, 2H), 7.67-7.52 (m, 5H), 7.36 (d, J = 2.0 Hz, 1H), 7.06 (dd, J = 8.3, 2.0 Hz, 1H), 4.23 (t, J = 7.3 Hz, 1H), 3.90 (s, 3H), 3.40 (dd, J = 13.9, 6.9 Hz, 1H), 3.29-3.23 (m, 1H) |
| 12 | (R)-2-trifluoromethylphenyl substituent | (R)-2-amino-N-(3-methoxy-4-(1H-pyrazol-4-yl)phenyl)-3-(2-(trifluoromethyl)phenyl)propanamide | 405.1 | A: 6.40  B: 7.09 | (400 MHz, methanol-d4) δ 8.07 (s, 2H), 7.77 (d, J = 7.2 Hz, 1H), 7.59-7.44 (m, 4H), 7.28 (d, J = 2.0 Hz, 1H), 6.99 (dd, J = 8.3, 2.0 Hz, 1H), 4.17 (dd, J = 9.5, 5.8 Hz, 1H), 3.89 (s, 3H), 3.42 (ddd, J = 23.7, 13.8, 7.7 Hz, 2H) |
| 13 | (R)-biphenyl substituent | (R)-3-([1,1'-biphenyl]-4-yl)-2-amino-N-(3-methoxy-4-(1H-pyrazol-4-yl)phenyl)propanamide | 413.1 | A: 7.37  B: 8.33 | (400 MHz, methanol-d4) δ 8.08 (s, 2H), 7.66-7.29 (m, 11H), 7.09 (dd, J = 8.3, 2.0 Hz, 1H), 4.23 (t, J = 7.3 Hz, 1H), 3.85 (d, J = 5.6 Hz, 3H), 3.35 (dd, J = 8.5, 5.3 Hz, 1H), 3.26-3.19 (m, 1H) |
| 14 | (R)-3,5-difluorophenyl substituent | (R)-2-amino-3-(3,5-difluorophenyl)-N-(3-methoxy-4-(1H-pyrazol-4-yl)phenyl)propanamide | 373.1 | A: 6.07  B: 6.69 | (400 MHz, methanol-d4) δ 8.08 (s, 2H), 7.56 (d, J = 8.3 Hz, 1H), 7.38 (d, J = 2.0 Hz, 1H), 7.09 (dd, J = 8.3, 2.0 Hz, 1H), 6.93 (ddd, J = 9.2, 7.6, 4.4 Hz, 3H), 4.22 (dd, J = 7.9, 6.7 Hz, 1H), 3.91 (s, 3H), 3.37-3.33 (m, 1H), 3.19 (dd, J = 14.0, 7.8 Hz, 1H) |

TABLE 1-continued

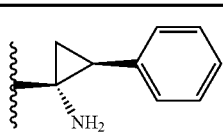

| Ex. | R | Name | LCMS (M + H)+ | HPLC Method, RT (min.) | 1H NMR |
|---|---|---|---|---|---|
| 15 | 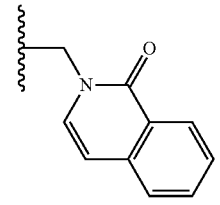 [SMILES: *Cn1ccc2ccccc2c1=O] | (1R,2S)-1-amino-N-(3-methoxy-4-(1H-pyrazol-4-yl)phenyl)-2-phenylcyclopropane-carboxamide | 349.1 | A: 5.53<br>B: 6.17 | (400 MHz, methanol-$d_4$) δ 7.98 (s, 2H), 7.44-7.27 (m, 6H), 6.65 (dd, J = 8.3, 2.0 Hz, 1H), 6.58 (d, J = 2.0 Hz, 1H), 3.77 (s, 3H), 3.08-2.98 (m, 1H), 2.71-2.61 (m, 1H), 1.89 (dd, J = 10.3, 8.2 Hz, 1H) |
| 16 | 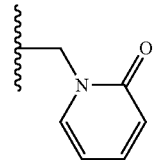 | N-(3-methoxy-4-(1H-pyrazol-4-yl)phenyl)-2-(1-oxoisoquinolin-2(1H)-yl)acetamide | 375.1 | A: 7.48<br>B: 7.19 | (400 MHz, DMSO) δ 10.39 (s, 1H), 8.21 (dd, J = 7.4, 4.3 Hz, 1H), 7.99 (s, 2H), 7.77-7.67 (m, 2H), 7.58-7.45 (m, 4H), 7.13 (dd, J = 8.4, 2.0 Hz, 1H), 6.66 (dd, J = 7.3, 2.0 Hz, 1H), 4.83 (s, 2H), 3.83 (s, 3H) |
| 17 | 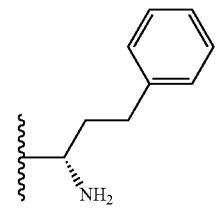 [SMILES: *[C@@H](N)CCc1ccccc1] | N-(3-methoxy-4-(1H-pyrazol-4-yl)phenyl)-2-(2-oxopyridin-1(2H)-yl)acetamide | 325.0 | A: 4.92<br>B: 5.35 | (400 MHz, DMSO) δ 10.37 (s, 1H), 8.01 (s, 2H), 7.67 (dd, J = 6.8, 1.7 Hz, 1H), 7.56 (d, J = 8.3 Hz, 1H), 7.52-7.43 (m, 2H), 7.12 (dd, J = 8.4, 1.9 Hz, 1H), 6.41 (d, J = 9.2 Hz, 1H), 6.26 (td, J = 6.7, 1.3 Hz, 1H), 4.75 (s, 2H), 3.83 (s, 3H) |
| 18 | 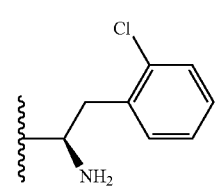 [SMILES: *[C@H](N)Cc1ccccc1Cl] | (S)-2-amino-N-(3-methoxy-4-(1H-pyrazol-4-yl)phenyl)-4-phenylbutanamide | 351.1 | A: 3.82<br>B: 4.93 | (400 MHz, methanol-$d_4$) δ 8.07 (s, 2H), 7.59 (d, J = 8.5 Hz, 1H), 7.49 (d, J = 2.0 Hz, 1H), 7.35-7.28 (m, 2H), 7.28-7.16 (m, 4H), 4.09 (t, J = 6.4 Hz, 1H), 3.95 (s, 3H), 2.86-2.76 (m, 2H), 2.39-2.17 (m, 2H) |
| 19 | 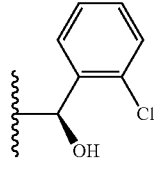 [SMILES: *[C@H](O)c1ccccc1Cl] | (R)-2-amino-3-(2-chlorophenyl)-N-(3-methoxy-4-(1H-pyrazol-4-yl)phenyl)propanamide | 371.15 | C: 1.22<br>D: 1.49 | (500 MHz, DMSO-$d_6$) δ 12.88 (br. s., 1H), 10.22 (br. s., 1H), 8.09 (br. s., 1H), 7.92 (br. s., 1H), 7.57 (d, J = 8.3 Hz, 1H), 7.49 (d, J = 7.7 Hz, 1H), 7.33 (d, J = 10.2 Hz, 3H), 7.23-7.14 (m, 2H), 7.13-6.95 (m, 2H), 4.09 (br. s., 1H), 3.83 (br. s., 3H), 3.29-3.13 (m, 2H) |
| 20 | | (R)-2-(2-chlorophenyl)-2-hydroxy-N-(3-methoxy-4-(1H-pyrazol-4-yl)phenyl)acetamide | 358.05 | C: 1.41<br>D: 1.44 | (500 MHz, DMSO-$d_6$) δ 10.06 (br. s., 1H), 8.00 (br. s., 2H), 7.60 (br. s., 2H), 7.55 (d, J = 6.9 Hz, 1H), 7.47 (d, J = 7.7 Hz, 1H), 7.42-7.31 (m, 3H), 6.70 (br. s., 1H), 5.49 (br. s., 1H), 3.84 (br. s., 3H) |

EXAMPLE 21

N-(2-(2-(Dimethylamino)ethoxy)-4-(1H-pyrazol-4-yl)phenyl)-2-phenylacetamide

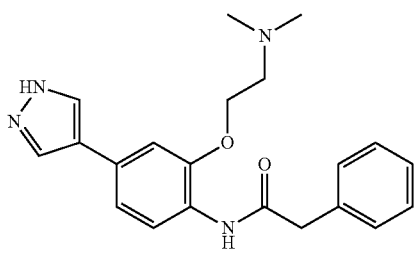 [SMILES: CN(C)CCOc1cc(-c2cn[nH]c2)ccc1NC(=O)Cc1ccccc1]

Example 21 was synthesized by following a similar procedure as described in Example 1 by replacing Intermediate 1 with Intermediate 4 and replacing (R)-2-((tert-butoxy carbonyl)amino)-4-phenylbutanoic acid with 2-phenylacetic acid in Example 1A. LCMS (ESI) m/z: 365.1 (M+H)$^+$; $^1$H NMR (400 MHz, methanol-$d_4$) δ 8.02 (d, J=1.8 Hz, 1H), 7.62-7.53 (m, 1H), 7.47-7.40 (m, 3H), 7.47-7.39 (m, 3H), 7.37-7.31 (m, 2H), 7.28 (d, J=8.0 Hz, 1H), 4.52-4.45 (m, 2H), 3.78 (s, 2H), 3.48-3.41 (m, 2H), 2.79 (s, 6H); Analytical HPLC RT=4.65 min (Method A), 5.94 min (Method B).

EXAMPLE 22

2-(2-Chlorophenyl)-N-(2-(2-(dimethylamino)ethoxy)-4-(1H-pyrazol-4-yl)phenyl)acetamide

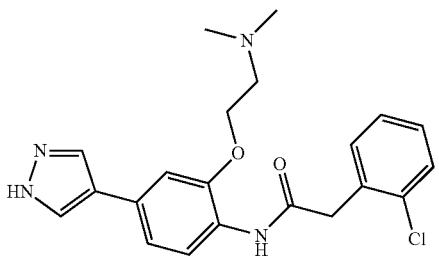 [SMILES: CN(C)CCOc1cc(-c2cn[nH]c2)ccc1NC(=O)Cc1ccccc1Cl]

Example 22 was synthesized by following a similar procedure as described in Example 21 by replacing 2-phenylacetic acid with 2-(2-chlorophenyl)acetic acid. LCMS (ESI) m/z: 399.0 (M+H)$^+$; $^1$H NMR (400 MHz, methanol-$d_4$) δ 8.03 (s, 2H), 7.63 (d, J=8.3 Hz, 1H), 7.48 (dd, J=5.8, 3.5 Hz, 2H), 7.39-7.32 (m, 3H), 7.28 (dd, J=8.3, 1.8 Hz, 1H), 4.59-4.50 (m, 2H), 3.98 (s, 2H), 3.62-3.50 (m, 2H), 2.89 (s, 6H); Analytical HPLC RT=4.93 min (Method A), 6.45 min (Method B).

EXAMPLE 23

N-(4-(1H-Pyrazol-4-yl)-2-(2-(pyrrolidin-1-yl)ethoxy)phenyl)-2-(2-chlorophenyl)acetamide

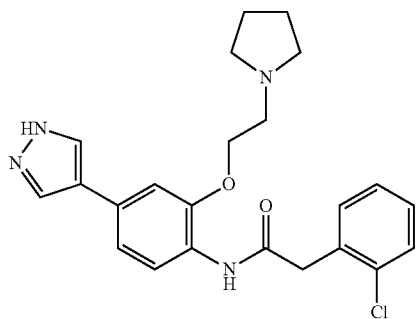 [SMILES: O=C(Cc1ccccc1Cl)Nc1ccc(-c2cn[nH]c2)cc1OCCN1CCCC1]

Example 23 was synthesized by following a similar procedure as described in Example 21 by replacing Intermediate 4 with Intermediate 5. LCMS (ESI) m/z: 425.1 (M+H)$^+$; $^1$H NMR (400 MHz, methanol-$d_4$) δ 8.04 (s, 2H), 7.58-7.43 (m, 3H), 7.42-7.24 (m, 4H), 4.60-4.49 (m, 2H), 3.99 (s, 2H), 3.64-3.44 (m, 4H), 3.09 (d, J=5.5 Hz, 2H), 2.16-1.72 (m, 4H); Analytical HPLC RT=5.34 min (Method A), 7.09 min (Method B).

EXAMPLE 24

(R)—N-(1-((3-Methoxy-4-(1H-pyrazol-4-yl)phenyl)amino)-1-oxo-4-phenylbutan-2-yl)benzamide

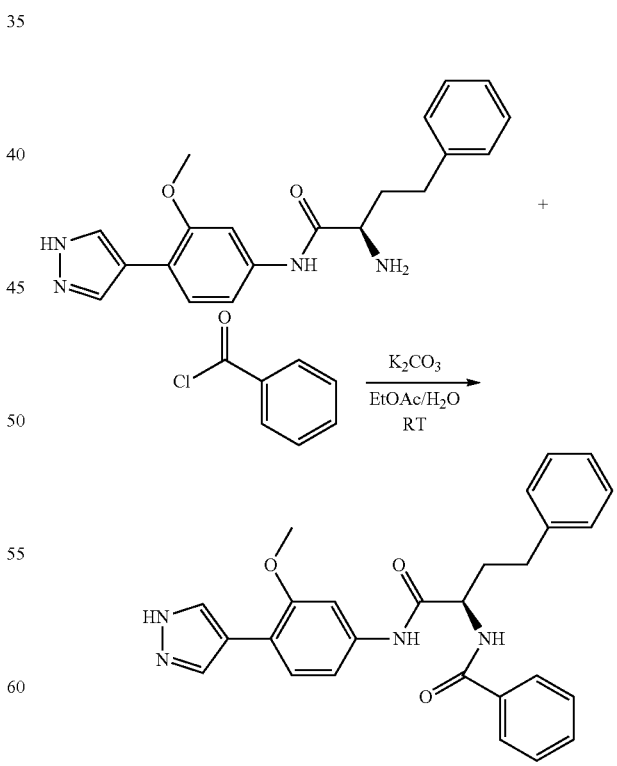

To a solution of Example 1 (20 mg, 0.043 mmol) in EtOAc (1.5 mL) were added 2M K$_2$CO$_3$ (0.054 mL, 0.108 mmol) and benzoyl chloride (5.99 μl, 0.052 mmol) at RT.

The reaction was stirred under argon at RT for 1 h. Solvent was removed. To the residue were added MeOH (1 mL) and NaOH (2M, 0.5 mL) and it was stirred at RT for 30 min. Purification by reverse phase chromatography afforded Example 24 (17 mg, 85% yield). LCMS (ESI) m/z: 455.25 (M+H)$^+$; $^1$H NMR (500 MHz, methanol-d$_4$) δ 7.96 (br. s., 2H), 7.88-7.80 (m, 2H), 7.62 (s, 2H), 7.58-7.52 (m, 1H), 7.51-7.44 (m, 4H), 7.31-7.22 (m, 4H), 7.21-7.15 (m, 1H), 7.12 (dd, J=8.3, 1.9 Hz, 1H), 4.78 (dd, J=8.3, 5.8 Hz, 1H), 3.93 (s, 3H), 2.89-2.72 (m, 2H), 2.43-2.16 (m, 2H); Analytical HPLC RT=1.64 min (Method C), 1.68 min (Method D).

EXAMPLE 25

(R)—N-(3-Methoxy-4-(1H-pyrazol-4-yl)phenyl)-2-(4-methylphenylsulfonamido)-4-phenylbutanamide

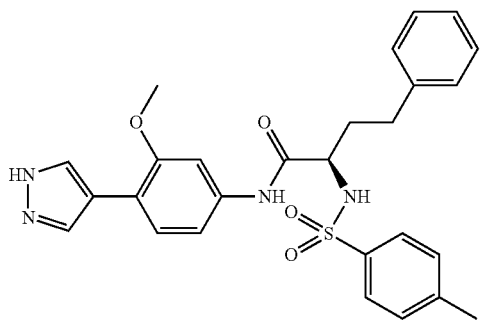 [SMILES: COc1cc(NC(=O)[C@@H](CCc2ccccc2)NS(=O)(=O)c2ccc(C)cc2)ccc1-c1cn[nH]c1]

Example 25 was prepared following a similar procedure as described in Example 24 by replacing benzoyl chloride with 4-methylbenzene-1-sulfonyl chloride. LCMS (ESI) m/z: 505.3 (M+H)$^+$; $^1$H NMR (500 MHz, methanol-d$_4$) δ 7.98 (br. s., 2H), 7.74 (d, J=8.3 Hz, 2H), 7.60 (s, 2H), 7.43 (d, J=8.3 Hz, 1H), 7.29-7.20 (m, 5H), 7.20-7.15 (m, 1H), 7.13 (d, J=7.4 Hz, 2H), 6.86 (dd, J=8.4, 1.8 Hz, 1H), 3.94-3.85 (m, 4H), 2.79-2.69 (m, 1H), 2.65-2.56 (m, 1H), 2.28 (s, 3H), 2.11-2.00 (m, 1H), 1.98-1.85 (m, 1H); Analytical HPLC RT=1.82 min (Method C), 1.88 min (Method D).

EXAMPLE 26

(R)-2-(Diethylamino)-N-(3-methoxy-4-(1H-pyrazol-4-yl)phenyl)-4-phenylbutanamide

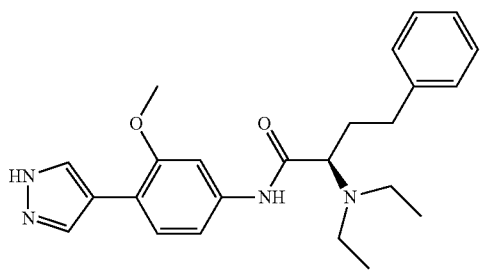 [SMILES: CCN(CC)[C@H](CCc1ccccc1)C(=O)Nc1ccc(-c2cn[nH]c2)c(OC)c1]

To a solution of Example 1 (20 mg, 0.043 mmol) in DCE (1.5 mL) were added NaBH(OAc)$_3$ (36.5 mg, 0.172 mmol) and acetaldehyde (9.49 mg, 0.215 mmol) at 0° C. The reaction was stirred under argon at RT for 1 h. Solvent was removed. Reverse phase chromatography afforded Example 26 (13.4 mg, 77% yield). LCMS (ESI) m/z: 407.30 (M+H)$^+$; $^1$H NMR (500 MHz, methanol-d$_4$) δ 7.97 (s, 2H), 7.62 (s, 2H), 7.55 (d, J=1.9 Hz, 1H), 7.51 (d, J=8.3 Hz, 1H), 7.32-7.27 (m, 2H), 7.26-7.22 (m, 2H), 7.22-7.16 (m, 1H), 7.02 (dd, J=8.4, 2.1 Hz, 1H), 3.96 (s, 3H), 3.42 (d, J=4.7 Hz, 1H), 2.97-2.86 (m, 1H), 2.74 (ddd, J=13.5, 9.0, 7.4 Hz, 3H), 2.67 (d, J=5.5 Hz, 2H), 2.26-2.11 (m, 1H), 2.02-1.89 (m, 1H), 1.08 (t, J=7.0 Hz, 6H); Analytical HPLC RT=1.18 min (Method C), 1.91 min (Method D).

EXAMPLE 27

(R)-2-Amino-N-(2-(2-(dimethylamino)ethoxy)-5-fluoro-4-(1H-pyrazol-4-yl)phenyl)-4-phenylbutanamide

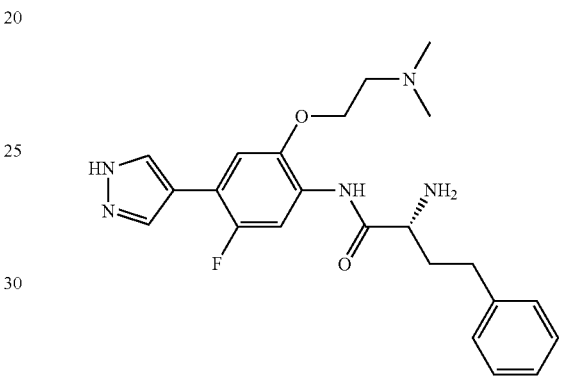

EXAMPLE 27A 2-(5-Bromo-4-fluoro-2-nitrophenoxy)-N,N-dimethylethanamine

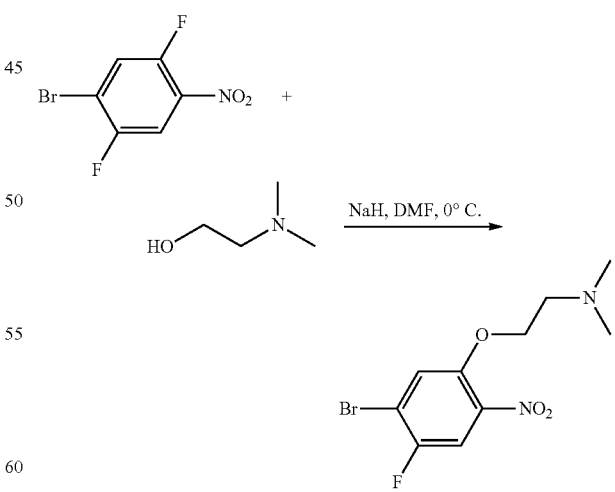

To a solution of 1-bromo-2,5-difluoro-4-nitrobenzene (515 mg, 2.164 mmol) in DMF (8 mL) were added 2-(dimethylamino)ethanol (0.261 mL, 2.60 mmol) and NaH (173 mg, 4.33 mmol) at 0° C. The reaction was stirred under argon at 0° C. for 1 hr. EtOAc was added to dilute the reaction followed by addition of NH₄Cl aq. solution to quench excess NaH. The reaction mixture was diluted with EtOAc, washed with H₂O and brine. The organic phase was dried over sodium sulfate, filtered and concentrated. The crude product was purified by normal phase chromatography to afford Example 27A as light yellow solid (523 mg, 79% yield). LCMS (ESI) m/z: 306.9/308.9 (M+H)⁺; ¹H NMR (400 MHz, chloroform-d) δ 7.70 (d, J=7.5 Hz, 1H), 7.33 (d, J=5.5 Hz, 1H), 4.18 (t, J=5.6 Hz, 2H), 2.79 (t, J=5.5 Hz, 2H), 2.35 (s, 6H).

EXAMPLE 27B

4-Bromo-2-(2-(dimethylamino)ethoxy)-5-fluoroaniline

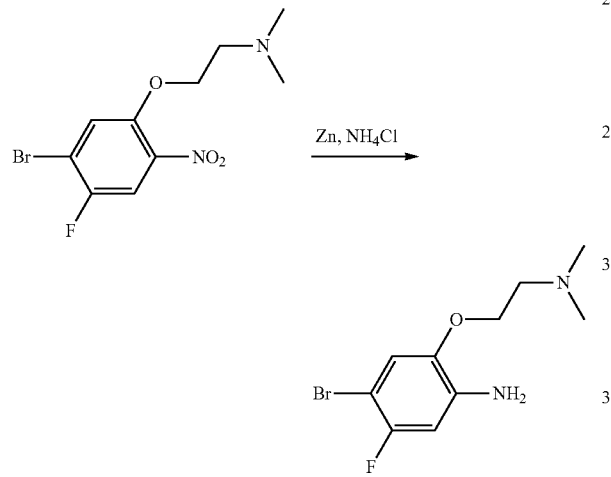

To a solution of Example 27A (523 mg, 1.703 mmol) in MeOH (15 mL) were added zinc powder (445 mg, 6.81 mmol) and NH₄Cl (547 mg, 10.22 mmol) at 0° C. The reaction was stirred under argon at RT for 3 hrs. Solid was filtered and solvent was removed to give dark solid as crude product of Example 27B (480 mg, 100% yield). LCMS (ESI) m/z: 276.9/278.9 (M+H)⁺.

EXAMPLE 27C (R)-tert-Butyl (1-((4-bromo-2-(2-(dimethylamino) ethoxy)-5-fluorophenyl)amino)-1-oxo-4-phenylbutan-2-yl)carbamate

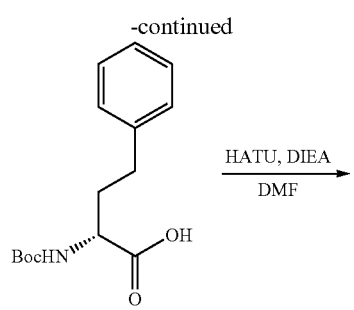

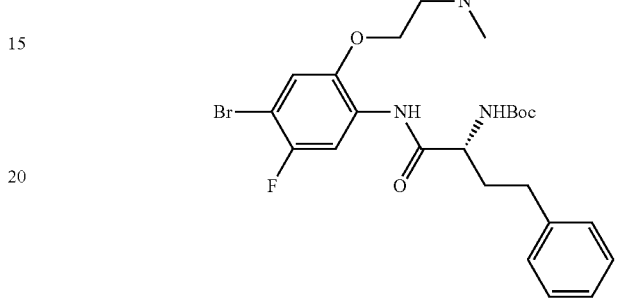

To a solution of Example 27B (80 mg, 0.289 mmol) in DMF (3 mL) were added (R)-2-((tert-butoxycarbonyl) amino)-4-phenylbutanoic acid (81 mg, 0.289 mmol), DIEA (0.101 mL, 0.577 mmol) and HATU (121 mg, 0.318 mmol) at RT. The reaction was stirred under argon at RT for 4 hrs. The reaction mixture was diluted with EtOAc, washed with H₂O and brine. The organic phase was dried over sodium sulfate, filtered and concentrated. The crude product was purified by normal phase chromatography to afford 27C as brown solid (101 mg, 65% yield). LCMS (ESI) m/z: 538.1/ 540.0 (M+H)⁺; ¹H NMR (400 MHz, methanol-d₄) δ 7.88 (d, J=10.1 Hz, 1H), 7.34 (d, J=6.2 Hz, 1H), 7.31-7.14 (m, 5H), 4.37 (t, J=4.5 Hz, 2H), 4.15 (dd, J=8.7, 5.4 Hz, 1H), 3.53 (br. s., 2H), 2.93 (s, 6H), 2.80-2.60 (m, 2H), 2.19-1.93 (m, 2H), 1.47 (s, 9H).

EXAMPLE 27

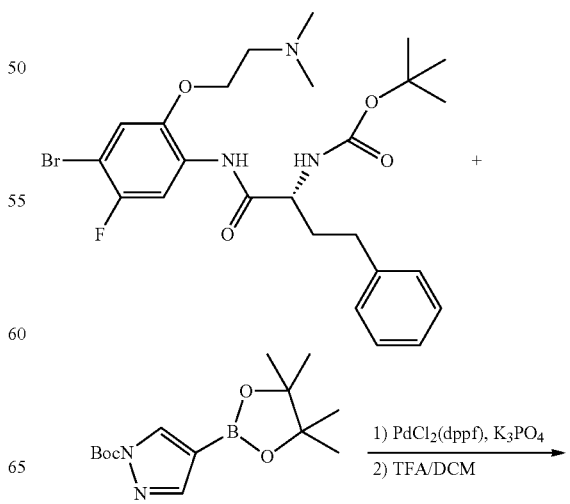

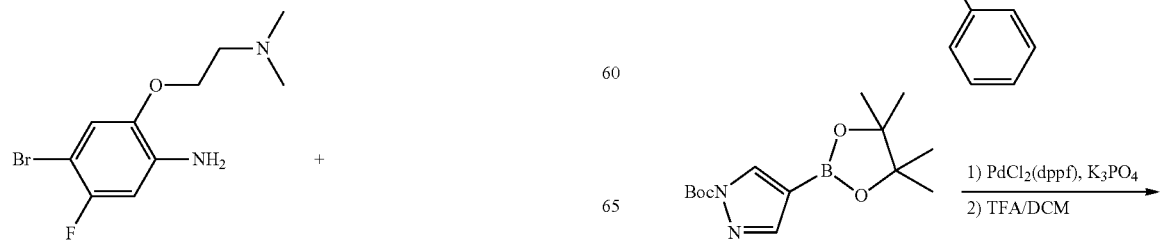

-continued

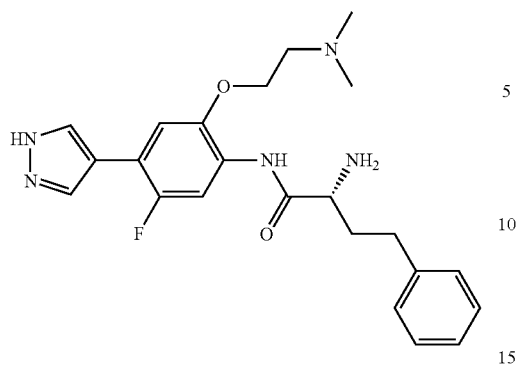

To a solution of 27C (101 mg, 0.188 mmol) in dioxane (5 mL) were added tert-butyl 4-(4,4,5,5-tetramethyl-1,3,2-dioxaborolan-2-yl)-1H-pyrazole-1-carboxylate (83 mg, 0.281 mmol), potassium phosphate (1M, 0.375 mL, 0.375 mmol) and $PdCl_2$(dppf)-$CH_2Cl_2$ (30.6 mg, 0.038 mmol) at RT. The reaction was stirred under argon at 90° C. for 1 hr and then was cooled to RT. The reaction mixture was diluted with EtOAc, washed with $H_2O$ and brine. The organic phase was dried over sodium sulfate, filtered and concentrated to give a crude product as dark brown solid (95 mg, 81% yield). LCMS (ESI) m/z: 626.3 (M+H)$^+$. To the intermediate (95 mg, 0.152 mmol) in DCM (3 mL) was added TFA (1 mL, 12.98 mmol) at RT. The reaction was stirred under argon at RT for 1 h. Solvent was removed under reduced pressure. Reverse phase chromatography afforded Example 27 (46.1 mg, 56% yield). LCMS (ESI) m/z: 426.25 (M+H)$^+$; $^1$H NMR (500 MHz, DMSO-$d_6$) δ 13.14 (br. s., 1H), 9.85 (br. s., 1H), 8.42 (br. s., 2H), 8.24-7.98 (m, 2H), 7.88 (d, J=12.4 Hz, 1H), 7.46 (d, J=6.9 Hz, 1H), 7.36-7.28 (m, 2H), 7.22 (d, J=7.2 Hz, 3H), 4.47 (br. s., 2H), 4.28 (br. s., 1H), 3.52 (br. s., 2H), 2.85 (br. s., 6H), 2.71 (t, J=8.3 Hz, 2H), 2.24-2.00 (m, 2H); Analytical HPLC RT=0.98 min (Method C), 1.23 min (Method D).

EXAMPLE 28

(R)—N-(4-(1H-Pyrazol-4-yl)phenyl)-2-amino-4-phenylbutanamide

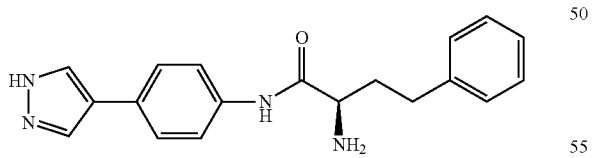

Example 28 was prepared following a similar procedure as described in Example 1 by replacing Intermediate 1 with Intermediate 3 in Example 1A. LCMS (ESI) m/z: 321.20 (M+H)$^+$; $^1$H NMR (500 MHz, DMSO-$d_6$) δ 12.93 (br. s., 1H), 10.50 (br. s., 1H), 8.34 (br. s., 2H), 8.13 (br. s., 1H), 7.92 (br. s., 1H), 7.61 (br. s., 4H), 7.31 (d, J=6.9 Hz, 2H), 7.23 (d, J=6.9 Hz, 3H), 4.03 (br. s., 1H), 2.69 (d, J=8.0 Hz, 2H), 2.13 (dd, J=15.0, 7.3 Hz, 2H); Analytical HPLC RT=1.19 min (Method C), 1.33 min (Method D).

EXAMPLE 29

N-(4-(1H-Pyrazol-4-yl)phenyl)-2-(2-chlorophenyl)acetamide

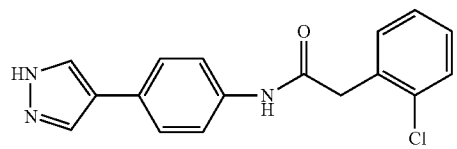 [SMILES: O=C(Cc1ccccc1Cl)Nc1ccc(-c2cn[nH]c2)cc1]

Example 29 was prepared following a similar procedure as described in Example 1 by replacing Intermediate 1 with Intermediate 3, and by replacing (R)-2-((tert-butoxycarbonyl)amino)-4-phenylbutanoic acid with 2-(2-chlorophenyl)acetic acid in Example 1A. LCMS (ESI) m/z: 312.10 (M+H)$^+$; $^1$H NMR (500 MHz, DMSO-$d_6$) δ 12.88 (br. s., 1H), 10.20 (br. s., 1H), 8.11 (br. s., 1H), 7.88 (br. s., 1H), 7.63-7.51 (m, 4H), 7.45 (t, J=7.7 Hz, 2H), 7.33 (d, J=4.4 Hz, 2H), 3.85 (br. s., 2H); Analytical HPLC RT=1.49 min (Method C), 1.52 min (Method D).

EXAMPLE 30

(R)-2-Amino-N-(3-methoxy-4-(3-methyl-1H-pyrazol-4-yl)phenyl)-4-phenylbutanamide

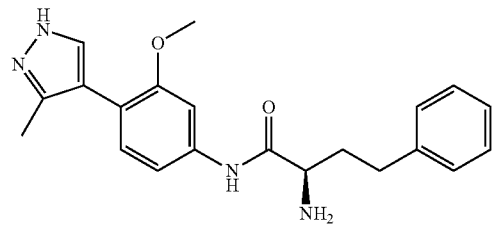 [SMILES: COc1cc(NC(=O)[C@H](N)CCc2ccccc2)ccc1-c1c[nH]nc1C]

EXAMPLE 30A (R)-tert-Butyl (1-((4-bromo-3-methoxyphenyl)amino)-1-oxo-4-phenylbutan-2-yl)carbamate

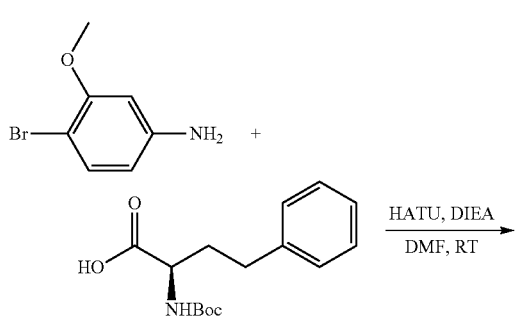

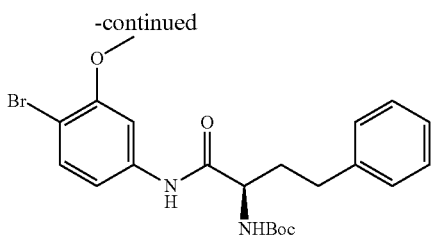

To a solution of (R)-2-((tert-butoxycarbonyl)amino)-4-phenylbutanoic acid (350 mg, 1.253 mmol) in DMF (5 mL) were added 4-bromo-3-methoxyaniline (253 mg, 1.253 mmol), HATU (500 mg, 1.316 mmol) and DIEA (0.438 mL, 2.506 mmol) at RT. The reaction was stirred under argon at RT for 1 hr. The reaction mixture was diluted with EtOAc, washed with $H_2O$ and brine. The organic phase was dried over sodium sulfate, filtered and concentrated. The crude product was purified by normal phase chromatography to afford Example 30A as light brown solid (531 mg, 91% yield). LCMS (ESI) m/z: 463.0/465.0 (M+H)$^+$; $^1$H NMR (400 MHz, chloroform-d) δ 8.95 (br. s., 1H), 7.36-7.22 (m, 4H), 7.21-7.11 (m, 3H), 6.78 (dd, J=8.6, 2.2 Hz, 1H), 5.39 (d, J=8.1 Hz, 1H), 4.30 (d, J=5.3 Hz, 1H), 3.79 (s, 3H), 2.86-2.64 (m, 2H), 2.29-2.11 (m, 1H), 2.04-1.93 (m, 1H), 1.46 (s, 9H).

EXAMPLE 30

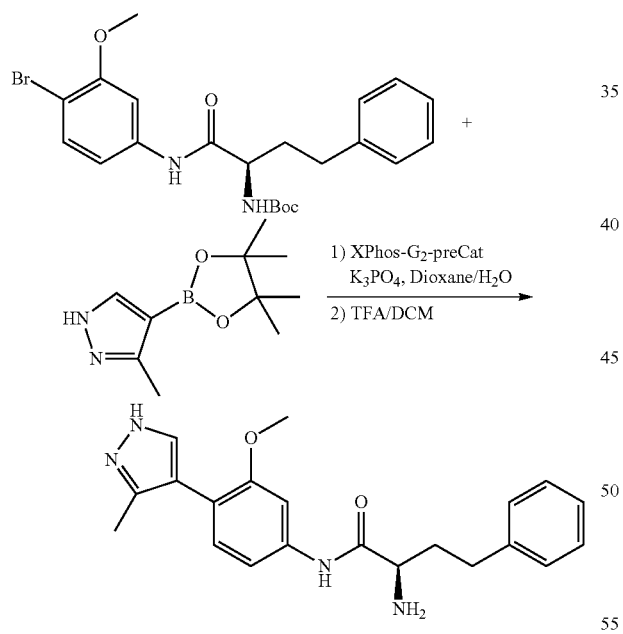

To a solution of Example 30A (20 mg, 0.043 mmol) in Dioxane (1.5 mL) were added 3-methyl-4-(4,4,5,5-tetramethyl-1,3,2-dioxaborolan-2-yl)-1H-pyrazole (13.47 mg, 0.065 mmol), potassium phosphate (1 M, 0.108 mL, 0.108 mmol) and chloro(2-dicyclohexylphosphino-2',4',6'-triisopropyl-1,1'-biphenyl)[2-(2'-amino-1,1'-biphenyl)]palladium (II) (2nd generation X-Phos-Precatalyst, 1.70 mg, 2.158 μmol) at RT. The reaction was stirred in a sealed vial at 85° C. for 1 h. The reaction was partitioned between EtOAc and water. Organic phase was separated and solvent was removed. To this residue was added DCM (1 mL) followed by addition of TFA (0.5 ml). After stirred at RT for 1 hr, solvent was removed. Purification by reverse phase chromatography afforded Example 30 (16.2 mg, 78% yield). LCMS (ESI) m/z: 365.1 (M+H)$^+$; $^1$H NMR (500 MHz, DMSO-d$_6$) δ 10.56 (s, 1H), 8.35 (br. s., 3H), 7.56 (br. s., 1H), 7.36-7.28 (m, 3H), 7.28-7.24 (m, 1H), 7.22 (d, J=4.4 Hz, 4H), 4.03 (br. s., 1H), 3.76 (s, 3H), 2.74-2.65 (m, 2H), 2.18 (s, 3H), 2.16-2.04 (m, 2H); Analytical HPLC RT=1.06 min (Method C), 1.25 min (Method D).

What is claimed is:

1. A compound having formula (III):

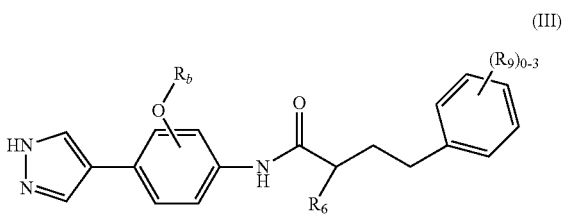

or an enantiomer, a diastereomer, a stereoisomer, a pharmaceutically acceptable salt thereof, wherein:

$R_6$ is independently selected from H, $C_{1-4}$alkyl substituted with 0-4 $R_e$, and $NR_aR_a$;

$R_9$, at each occurrence, is independently selected from F, Cl, Br, and $C_{1-4}$ alkyl substituted with 0-4 $R_e$;

$R_a$, at each occurrence, is independently selected from H, CN, $C_{1-6}$ alkyl substituted with 0-5 $R_e$, $C_{2-6}$ alkenyl substituted with 0-5 $R_e$, $C_{2-6}$ alkynyl substituted with 0-5 $R_e$, —(CH$_2$)$_r$—C$_{3-10}$carbocyclyl substituted with 0-5 $R_e$, and —(CH$_2$)$_r$-heterocyclyl substituted with 0-5 $R_e$;

$R_b$ is independently selected from H and $C_{1-6}$ alkyl substituted with 0-5 $R_e$;

Re, at each occurrence, is independently selected from $C_{1-6}$ alkyl substituted with 0-5 $R_f$, $C_{2-6}$ alkenyl, $C_{2-6}$ alkynyl, —(CH$_2$)$_r$—C$_{3-6}$ cycloalkyl, F, Cl, Br, CN, NO$_2$, =O, CO$_2$H, —(CH$_2$)$_r$OC$_{1-5}$ alkyl, —(CH$_2$)$_r$OR$_f$, S(O)$_p$R$_f$, S(O)$_p$NR$_f$R$_f$, and —(CH$_2$)$_r$NR$_f$R$_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

2. A compound having formula (V):

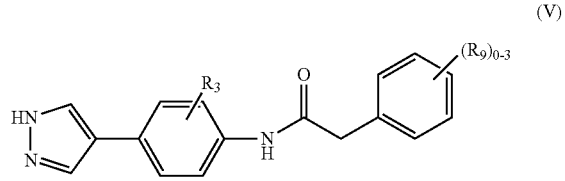

or an enantiomer, a diastereomer, a stereoisomer, a pharmaceutically acceptable salt thereof, wherein:

$R_3$ is —OR$_b$;

$R_9$, at each occurrence, is independently selected from F, Cl, Br, $C_{1-4}$ alkyl substituted with 0-4 $R_e$;

$R_b$ is independently selected from H, $C_{1-6}$ alkyl substituted with 0-5 $R_e$, —$(CH_2)_r$—$C_{3-10}$ carbocyclyl substituted with 0-5 $R_e$, and —$(CH_2)_r$-heterocyclyl substituted with 0-5 $R_e$;

$R_e$, at each occurrence, is independently selected from $C_{1-6}$ alkyl substituted with 0-5 $R_f$, $C_{2-6}$ alkenyl, $C_{2-6}$ alkynyl, —$(CH_2)_r$—$C_{3-6}$ cycloalkyl, F, Cl, Br, CN, $NO_2$, =O, $CO_2H$, —$(CH_2)_rOC_{1-5}$ alkyl, —$(CH_2)_rOR_f$, $S(O)_pR_f$, $S(O)_pNR_fR_f$, and —$(CH_2)_rNR_fR_f$;

$R_f$, at each occurrence, is independently selected from H, $C_{1-5}$ alkyl, $C_{3-6}$ cycloalkyl, and phenyl, or $R_f$ and $R_f$ together with the nitrogen atom to which they are both attached form a heterocyclic ring optionally substituted with $C_{1-4}$alkyl;

p, at each occurrence, is independently selected from zero, 1, and 2; and r, at each occurrence, is independently selected from zero, 1, 2, 3, and 4.

3. A compound according to Formula (VI):

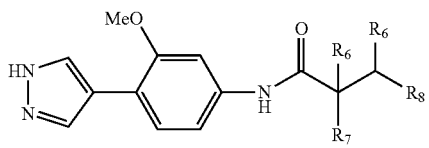

(VI)

or an enantiomer, a diastereomer, a stereoisomer, a pharmaceutically acceptable salt thereof, wherein:

$R_6$ is H or two adjacent $R_6$ groups form a cycloalkyl;
$R_7$ is independently selected from $NH_2$ or OH; and
$R_8$ is independently selected from

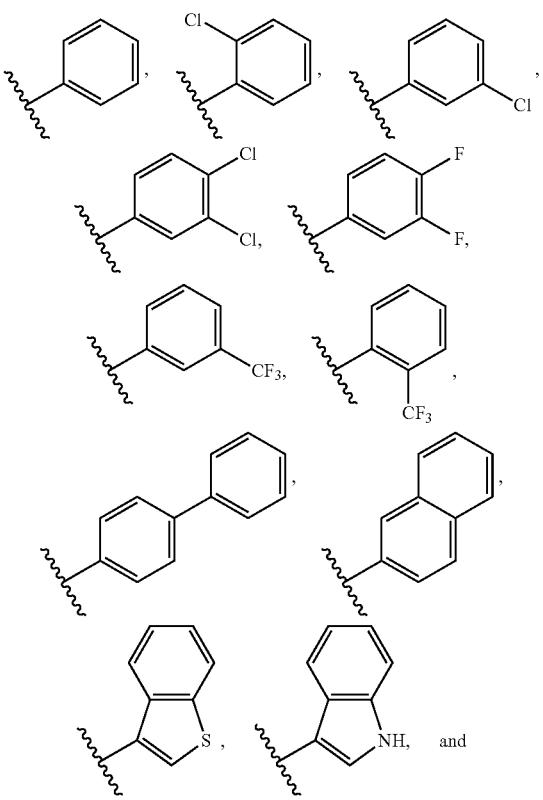

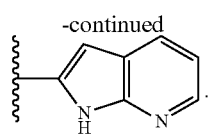

4. A pharmaceutical composition comprising one or more compounds according to claim 1 and a pharmaceutically acceptable carrier or diluent.

5. A compound selected from
(R)-2-Amino-N-(3-methoxy-4-(1H-pyrazol-4-yl)phenyl)-4-phenylbutanamide,
2-(2-chlorophenyl)-N-(3-methoxy-4-(1H-pyrazol-4-yl)phenyl)acetamide,
(R)-2-amino-2-(2-chlorophenyl)-N-(3-methoxy-4-(1H-pyrazol-4-yl)phenyl)acetamide,
(+/−)-2-(2-chlorophenyl)-N-(3-methoxy-4-(1H-pyrazol-4-yl)phenyl)propanamide,
(R)-2-amino-3-(3,4-dichlorophenyl)-N-(3-methoxy-4-(1H-pyrazol-4-yl)phenyl) propanamide,
(R)-2-amino-N-(3-methoxy-4-(1H-pyrazol-4-yl)phenyl)-3-(naphthalen-2-yl)propanamide,
(R)-2-amino-3-(1H-indol-3-yl)-N-(3-methoxy-4-(1H-pyrazol-4-yl)phenyl)propanamide,
(R)-2-amino-N-(3-methoxy-4-(1H-pyrazol-4-yl)phenyl)-3-phenylpropanamide,
(S)-2-amino-3-(benzo[b]thiophen-3-yl)-N-(3-methoxy-4-(1H-pyrazol-4-yl)phenyl) propanamide,
(+/−)-2-amino-N-(3-methoxy-4-(1H-pyrazol-4-yl)phenyl)-3-(1H-pyrrolo[2,3-b]pyridin-2-yl)propanamide,
(R)-2-amino-N-(3-methoxy-4-(1H-pyrazol-4-yl)phenyl)-3-(3-(trifluoromethyl)phenyl) propanamide,
(R)-2-amino-N-(3-methoxy-4-(1H-pyrazol-4-yl)phenyl)-3-(2-(trifluoromethyl)phenyl) propanamide,
(R)-3-([1,1'-biphenyl]-4-yl)-2-amino-N-(3-methoxy-4-(1H-pyrazol-4-yl)phenyl)propanamide,
(R)-2-amino-3-(3,5-difluorophenyl)-N-(3-methoxy-4-(1H-pyrazol-4-yl)phenyl) propanamide,
(1R,2S)-1-amino-N-(3-methoxy-4-(1H-pyrazol-4-yl)phenyl)-2-phenylcyclopropanecarboxamide,
N-(3-methoxy-4-(1H-pyrazol-4-yl)phenyl)-2-(1-oxoisoquinolin-2(1H)-yl)acetamide,
N-(3-methoxy-4-(1H-pyrazol-4-yl)phenyl)-2-(2-oxopyridin-1(2H)-yl)acetamide,
(S)-2-amino-N-(3-methoxy-4-(1H-pyrazol-4-yl)phenyl)-4-phenylbutanamide,
(R)-2-amino-3-(2-chlorophenyl)-N-(3-methoxy-4-(1H-pyrazol-4-yl)phenyl)propanamide,
(R)-2-(2-chlorophenyl)-2-hydroxy-N-(3-methoxy-4-(1H-pyrazol-4-yl)phenyl)acetamide,
N-(2-(2-(Dimethylamino)ethoxy)-4-(1H-pyrazol-4-yl)phenyl)-2-phenylacetamide,
2-(2-Chlorophenyl)-N-(2-(2-(dimethylamino)ethoxy)-4-(1H-pyrazol-4-yl)phenyl)acetamide,
N-(4-(1H-Pyrazol-4-yl)-2-(2-(pyrrolidin-1-yl)ethoxy)phenyl)-2-(2-chlorophenyl)acetamide,
(R)-N-(1-((3-Methoxy-4-(1H-pyrazol-4-yl)phenyl)amino)-1-oxo-4-phenylbutan-2-yl)benzamide,
(R)-N-(3-Methoxy-4-(1H-pyrazol-4-yl)phenyl)-2-(4-methylphenylsulfonamido)-4-phenylbutanamide,
(R)-2-(Diethylamino)-N-(3-methoxy-4-(1H-pyrazol-4-yl)phenyl)-4-phenylbutanamide,
(R)-2-Amino-N-(2-(2-(dimethylamino)ethoxy)-5-fluoro-4-(1H-pyrazol-4-yl)phenyl)-4-phenylbutanamide,
(R)-N-(4-(1H-Pyrazol-4-yl)phenyl)-2-amino-4-phenylbutanamide, N-(4-(1H-Pyrazol-4-yl)phenyl)-2-(2-chlorophenyl)acetamide, (R)-2-Amino-N-(3-methoxy-4-(3-methyl-1H-pyrazol-4-yl)phenyl)-4-phenylbutanamide, or a pharmaceutically acceptable salt thereof.

* * * * *